United States Patent
Rhodes et al.

(10) Patent No.: US 10,269,450 B2
(45) Date of Patent: Apr. 23, 2019

(54) PROBABILISTIC EVENT CLASSIFICATION SYSTEMS AND METHODS

(71) Applicant: Quantros, Inc., Greenville, SC (US)

(72) Inventors: Bryn Thomas Rhodes, Orem, UT (US); Randal Earl Childers, Campbell, CA (US); Gerard Francis Livaudais, Kihei, HI (US); Stefanie Fenton, Reno, NV (US); Tim Thompson, Delevan, NY (US); Sandra Foley, San Jose, CA (US); Jeffrey Greene, San Francisco, CA (US)

(73) Assignee: Quantros, Inc., Greenville, SC (US)

( * ) Notice: Subject to any disclaimer, the term of this patent is extended or adjusted under 35 U.S.C. 154(b) by 0 days.

(21) Appl. No.: 14/284,329

(22) Filed: May 21, 2014

(65) Prior Publication Data
US 2014/0350964 A1    Nov. 27, 2014

Related U.S. Application Data

(60) Provisional application No. 61/826,428, filed on May 22, 2013.

(51) Int. Cl.
*G06F 19/00* (2018.01)
*G16H 40/20* (2018.01)

(52) U.S. Cl.
CPC .......... *G16H 40/20* (2018.01); *G06F 19/00* (2013.01)

(58) Field of Classification Search
CPC ...... G06Q 50/22; G06Q 50/24; G06F 19/345; G06F 19/3443; G06F 19/322; G06F 19/326; G06F 19/3487
USPC ......................................................... 705/2–3
See application file for complete search history.

(56) References Cited

U.S. PATENT DOCUMENTS

| | | | |
|---|---|---|---|
| 6,842,769 B1 | 1/2005 | Kim et al. | |
| 6,952,695 B1 * | 10/2005 | Trinks et al. | |
| 6,957,249 B2 | 10/2005 | Salo et al. | |
| 7,039,594 B1 | 5/2006 | Gersting | |
| 7,043,566 B1 | 5/2006 | Grant et al. | |
| 7,325,042 B1 | 1/2008 | Soscia et al. | |
| 7,734,656 B2 | 6/2010 | Bessette et al. | |
| 8,694,335 B2 * | 4/2014 | Yegnanarayanan | .... G16H 10/60 705/2 |

(Continued)

FOREIGN PATENT DOCUMENTS

WO    WO2014190092 A1    7/2014

OTHER PUBLICATIONS

International Search Report dated Sep. 24, 2014 for Application No. PCT/US2014/039035 filed May 21, 2014, 15 pages.

(Continued)

*Primary Examiner* — Dilek B Cobanoglu
(74) *Attorney, Agent, or Firm* — Carr & Ferrell LLP

(57) ABSTRACT

Probabilistic event classifications systems and method are provided herein. In one embodiment, a method includes receiving an event narrative, the event narrative comprising textual content describing a safety event, parsing the textual content to identify key terms, searching a safety event database for classifications associated with the key terms, selecting a set of classifications based on the key terms using statistical analysis, the set of classifications comprising potential event types for the event narrative, and displaying the set of classifications for the event narrative via a graphical user interface.

14 Claims, 37 Drawing Sheets

(56) References Cited

U.S. PATENT DOCUMENTS

| | | | |
|---|---|---|---|
| 2003/0154208 A1* | 8/2003 | Maimon et al. | 707/100 |
| 2003/0171953 A1 | 9/2003 | Narayanan et al. | |
| 2005/0010440 A1 | 1/2005 | Merkin et al. | |
| 2005/0033761 A1 | 2/2005 | Guttman et al. | |
| 2005/0071309 A1 | 3/2005 | Ustaris | |
| 2005/0138111 A1 | 6/2005 | Aton et al. | |
| 2005/0187797 A1 | 8/2005 | Johnson | |
| 2005/0192838 A1 | 9/2005 | Jones et al. | |
| 2005/0216314 A1 | 9/2005 | Secor | |
| 2005/0222870 A1 | 10/2005 | Schumann et al. | |
| 2005/0262039 A1 | 11/2005 | Kreulen et al. | |
| 2006/0031018 A1 | 2/2006 | Bush et al. | |
| 2006/0068368 A1 | 3/2006 | Mohler et al. | |
| 2006/0178908 A1 | 8/2006 | Rappaport | |
| 2006/0184560 A1 | 8/2006 | Indjic | |
| 2006/0190298 A1 | 8/2006 | Nigmann et al. | |
| 2006/0206361 A1 | 9/2006 | Logan | |
| 2006/0287890 A1* | 12/2006 | Stead et al. | 705/3 |
| 2006/0288286 A1 | 12/2006 | Chandler et al. | |
| 2007/0016450 A1 | 1/2007 | Bhora et al. | |
| 2007/0021987 A1* | 1/2007 | Binns et al. | 705/4 |
| 2007/0033073 A1 | 2/2007 | Tajaliawal et al. | |
| 2007/0130105 A1 | 6/2007 | Papatla | |
| 2007/0239484 A1 | 10/2007 | Arond et al. | |
| 2008/0052205 A1 | 2/2008 | Dolley et al. | |
| 2008/0065680 A1 | 3/2008 | Moon et al. | |
| 2008/0133290 A1 | 6/2008 | Siegrist et al. | |
| 2008/0139889 A1 | 6/2008 | Bagan | |
| 2008/0263055 A1 | 10/2008 | Kumar et al. | |
| 2009/0076847 A1* | 3/2009 | Gogolak | 705/2 |
| 2009/0228777 A1 | 9/2009 | Henry et al. | |
| 2009/0281831 A1 | 11/2009 | Richards et al. | |
| 2009/0327269 A1* | 12/2009 | Paparizos et al. | 707/5 |
| 2011/0082712 A1* | 4/2011 | Eberhardt et al. | 705/4 |
| 2012/0197896 A1 | 8/2012 | Li et al. | |
| 2012/0215560 A1 | 8/2012 | Ofek et al. | |
| 2012/0330946 A1 | 12/2012 | Arredondo et al. | |
| 2013/0110498 A1* | 5/2013 | Bekkerman | 704/9 |
| 2013/0144641 A1 | 6/2013 | Bessette | |
| 2014/0129260 A1* | 5/2014 | Kang | G06Q 50/22 705/3 |
| 2014/0207477 A1 | 7/2014 | Forthman | |
| 2014/0207478 A1 | 7/2014 | Forthman | |

OTHER PUBLICATIONS

Appendix to U.S. Appl. No. 11/962,062, filed Dec. 20, 2007, pp. 1-134.

Forthman, M. Thane et al., "Risk-Adjusted Indices for Measuring the Quality of Inpatient Care," Qmanage Health Care, vol. 19, No. 3, 2010, pp. 265-277, 13 pages.

U.S. Appl. No. 14/159,162, filed Jan. 20, 2014, 19 pages.

U.S. Appl. No. 14/159,171, filed Jan. 20, 2014, 19 pages.

* cited by examiner

PROBABILISTIC EVENT CLASSIFICATION SYSTEMS AND METHODS

CROSS REFERENCE TO RELATED APPLICATIONS

This application claims the benefit of U.S. Provisional Application No. 61/826,428, filed May 22, 2013, which is hereby incorporated by reference herein in its entirety, including all reference cited therein.

FIELD OF THE INVENTION

The present technology may be generally described as providing event classification. More specifically, but not by way of limitation, the present technology provides event classification for events involving patient safety.

SUMMARY

In some embodiments, the present technology is directed to a method for classifying an event narrative using a classification system comprising a processor and a memory for storing executable instructions, the processor being configured to execute the instructions to perform the method, comprising: (a) receiving an event narrative, the event narrative comprising textual content describing a safety event; (b) parsing the textual content to identify key terms; (c) searching a safety event database for classifications associated with the key terms; (d) selecting a set of classifications based on the key terms using statistical analysis, the set of classifications comprising potential event types for the event narrative; and (e) displaying the set of classifications for the event narrative via a graphical user interface.

In some embodiments, the present technology is directed to a method for classifying an event narrative using a classification system comprising a processor and a memory for storing executable instructions, the processor being configured to execute the instructions to perform the method, comprising: (a) receiving an event narrative, the event narrative comprising textual content describing a safety event; (b) processing the textual content to identify semantic concepts within the textual content; (c) generating a representation based on the semantic concepts; (d) searching the safety event database for classifications having semantic concepts similar to the representation; (e) selecting a set of classifications based on the representation using semantic analysis; and (f) displaying the set of potential event types for the event narrative via a graphical user interface.

In some embodiments, the present technology is directed to a method for classifying an event narrative using a classification system comprising a processor and a memory for storing executable instructions, the processor being configured to execute the instructions to perform the method, comprising: (a) receiving an event narrative, the event narrative comprising textual content describing a safety event, the safety event being an incident that has the potential to cause an adverse effect to a patient; (b) parsing the textual content to identify key terms within the textual content, the key terms being linked to classifications for the event narrative, the classifications being stored in a safety event database; (c) searching the safety event database for classifications that match the key terms parsed from the textual content; (d) selecting a set of classifications based on the key terms using natural language processing analysis; and (e) displaying the set of potential event types for the event narrative via a graphical user interface.

BRIEF DESCRIPTION OF THE DRAWINGS

Certain embodiments of the present technology are illustrated by the accompanying figures. It will be understood that the figures are not necessarily to scale and that details not necessary for an understanding of the technology or that render other details difficult to perceive may be omitted. It will be understood that the technology is not necessarily limited to the particular embodiments illustrated herein.

FIG. 30 is an exemplary GUI generated by the system of FIG. 1 that illustrates inferred suggestions for classification for the narrative text;

DESCRIPTION OF EXEMPLARY EMBODIMENTS

Figure 1:
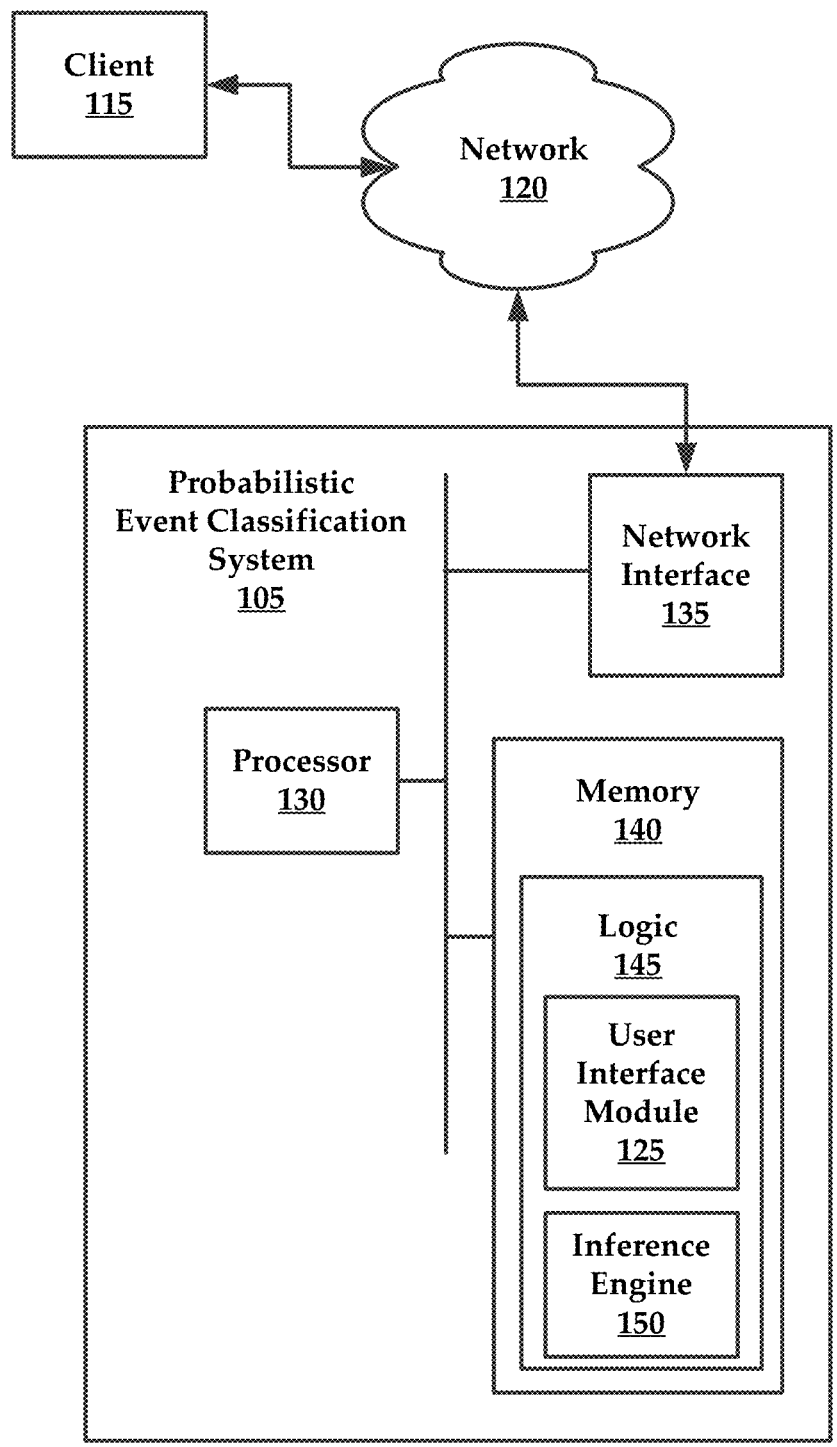
FIG. 1 is an exemplary system architecture that can be used to practice aspects of the present technology.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

Generally speaking, the present technology may include various systems and methods that provide probabilistic event characteristic inference functionalities. Various models have been used to evaluate the feasibility of described systems and processes. These models will be described in greater detail with reference to FIGS. 2-28, which will be described in greater detail herein.

FIG. 1 illustrates an exemplary architecture for practicing aspects of the present technology. The architecture comprises a probabilistic event classification system, hereinafter "system 105" that is configured to classify events using text tokenization and probability calculations, as well as other processes which will be described in greater detail infra. Generally the system 105 is configured to communicate with client devices, such as client 115. The client 115 may include, for example, a Smartphone, a laptop, a computer, or other similar computing device. An example of a computing device that can be utilized in accordance with the present invention is described in greater detail with respect to FIG. 35.

The system 105 may communicatively couple with the client 115 via a public or private network, such as network 120. Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 120 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking.

The system 105 generally comprises a processor, 130, a network interface 135, and a memory 140. According to some embodiments, the memory 140 comprises logic (e.g., instructions or applications) 145 that can be executed by the processor 130 to perform various methods. For example, the logic may include a user interface module 125 as well as an inference engine 150 that is configured to provide the statistical and probabilistic calculations described in greater detail herein, as well as the inference of classifications from these calculated values.

For context and clarity, some definitions and supporting descriptions are provided below. The system 105 leverages the large body of historical event data with associated narrative texts that have already been classified, which is referred to herein as a "training corpus". This data set can be used by the system 105 to calculate statistics regarding the number of appearances of tokens within the narrative text for each classification.

These statistics can then be used by the system 105 to calculate probabilities that the appearance of a given token within the narrative text for a new event determines the classification of the event. Event characteristics can include, but are not limited to, "Event Type", which is often the broadest category of classification of the event. "Nature" is a further classification information within an Event Type. To be sure, the same Nature may appear in any number of Event Types, so the relationship is not strictly a hierarchy, but rather a network relationship or mapping, although in some instances the relationship may by strictly hierarchical. "Sub-Nature" is a further classification within a Nature. It will be understood that, in contrast to the relationship between Event Type and Nature, the relationship between Nature and Sub-Nature may (or may not) be specifically hierarchical. "Care Setting" is the care setting for an event that specifies the overall type of facility in which the event occurred, such as Acute Care, Inpatient, Outpatient, and so forth. "Department" includes a specific department for an event that specifies a specific subcategory of care setting in which the event occurred. To be sure, the department references a department type, not specific instances of departments within an organization.

"Geographical Location" is a physical region in which the event occurred. Assuming this information can be obtained historically, it may be used by the system 105 for analyzing various types of statistics and creating more robust refined calculations.

"Tokenization" can be broadly defined as the process of dividing a text narrative into smaller text segments called "tokens." The tokens may include words, groups of words, or phrases. Algorithms may be used to identify tokens from an event narrative, including algorithms that identify spaces or punctuation in text. The tokens, once identified using tokenization, may be used for subsequent search or processing as described below.

The system 105 may utilize the following types of tokenization, which are listed below in increasing order of potential complexity. Straight tokenization is a process whereby each individual word within the narrative text will be considered a single token for the purposes of gathering metrics. Nary tokenization is a process whereby in addition to each individual word, the system may take the word and the next word, as well as the word and the next two words, up to some arbitrary position N, with sentence terminators stopping tokenization. Keyword tokenization is a process whereby in addition to capturing each individual word, a dictionary of medical terms could be used to attach significance to key terms within the narrative text. This significance could serve as a weighting factor in the probability determination.

The system 105 herein may rely, in some instances, on various metrics that can be calculated for events. For each token, the system 105 may capture the frequency of appearance of that token for each Event Type, Nature, and Sub-Nature.

In addition, the system 105 may analyze metrics along any or all of the following dimensions: (i) Care Setting; (ii) Department; (iii) Geographical Location; (iv) Nature within Event Type; (v) Sub-Nature within Event Type and/or Nature; (vi) Sub-Nature within Nature; and (vii) Event Type within Nature and/or Sub-Nature. These metrics may be used by the system 105 to investigate potential correlations between tokens along these dimensions, which may in turn inform the decision about which method of tokenization to use.

For each characteristic, a set of tokens may appear with relatively high frequency on that characteristic, and not on any other characteristic. Of course, this partitioning will not necessarily be disjointed in nature, but in general, the higher the frequency of a given token for a specific characteristic, relative to the other characteristics, the higher the probability that the appearance of that token indicates that characteristic.

In this way, common words such as 'of' and 'the' will naturally not contribute to any particular characteristic in these embodiments, because they may occur with relatively equal frequency on all characteristics. Thus, the system 105 may be configured to ignore these common words, as well as punctuation and other words or groups of characters which possess little or no significance contextually.

Broadly speaking, the system 105 performs various operations which seek to answer the question: "Given the narrative text for an unclassified event, what are the most likely N classifications for the event?" With the definitions provided below, the system 105 can be configured to tokenize the narrative text for the input event. That is, the system 105 tokenizes the input text for an event, such as when a healthcare professional enters free form text into a text input UI generated by the system 105.

After receiving the free form text, the system 105 may locate the top N most interesting tokens for each characteristic, where "interesting" is defined as most frequently appearing tokens. These tokens may be referred to as "potential characteristics of interest". For each potential characteristic of interest, the system 105 may use a frequency distribution of the tokens of interest contributing to the characteristic across all characteristics to compute a probability for the characteristic.

The system 105 then returns top M characteristics of interest, which are ranked according to priority (e.g., importance).

In a more specific example of a method, the system 105 may generate tokens from textual content included in an event narrative, and determine tokens that appear most frequently in the event narrative. In some embodiments the system 105 may be configured to calculate probabilities for a plurality of characteristics for the event narrative using a frequency distribution of the frequently appearing tokens across a plurality of characteristics of a training corpus. Also, the system 105 may be configured to infer a set of potential classifications for the event narrative based upon the calculated probabilities for the plurality of characteristics, as well as display the set of potential classifications for the event narrative via a graphical user interface. These functions are merely descriptive of an example configuration of the system 105 and it will be appreciated that the system 105 may be configured to provide additional or fewer operations that those discussed above. Additional details regarding each of the aforementioned functions or operations will be described in greater detail below.

Advantageously, the system 105 provides users with the ability to enter safety event data quickly. During that process the event may not only be captured by the system 105, but classified in terms of the type of event that occurred. This classification may occur based on a taxonomy including three main levels: (1) Event Type; (2) Nature; and (3) Sub-Nature. These characteristics may be selected by the user in order to capture the classification of the event.

With respect to manual selections of event type, one of the biggest problems facing a user is deciding which classification is appropriate for a given event. This problem is further complicated by the fact that often, the Event Type level is too broad to provide the user with enough cues to guide the selection to the appropriate Nature and Sub-Nature.

Rather than present the classification problem in this way, the system 105 uses historical event data to infer the most likely classification (or classifications) for an event based on statistical probability of the appearance of terms within the event narrative. These most likely classifications can then be suggested to the user for confirmation or further refinement.

In accordance with the present disclosure, the system 105 may rely on several assumptions in order to allow the data analysis to guide the determination of the likeliest model for characteristic inference. The system 105 may be configured to assume no correlation between tokens within the narrative text. This simplification seeks to determine whether simple tokenization of the narrative text will be enough to yield confident results. Next, the system 105 is configured to assume no correlation between Event Type, Nature, and Sub-Nature. This simplification seeks to determine whether the simplest possible statistical distribution and probability calculation will be sufficient to yield confident results. The system 105 may also be configured to ignore token equivalence. This simplification seeks to determine whether the approach would be sufficient to yield confidence even without considering things like spelling errors and synonyms.

The system 105 may also be configured to consider the probability of misclassification of tokens. Given that the training corpus of events being used to compute the data may be hand classified, the system 105 assume that a portion of the events being used within the training corpus have been misclassified and thus affect the overall calculation of statistics. This probability may be incorporated into the probability calculation defined above.

The values for this probability can be determined using statistical methods (i.e. expert reclassification of random sampling). This probability can then provide a starting point for the probability of misclassification that may be input by the system 105. Note that this probability may also be a potential tuning parameter used by the system 105 to create, for example, ranges of possible calculations that account for different assumptions with regard to misclassifications. For example, one set of statistics can be calculated if the system 105 assumes that four percent of the training corpus has been mislabeled, while a second set of statistics can be calculated if the system 105 assumes that one percent of the training corpus has been mislabeled. These parameters can be established from empirical analyses of historical data, or can be selected by the end user.

In some instances, the system 105 may employ a modified approach to the method above by allowing for token equivalence to account for spelling errors, synonyms, and equivalent medical terms—just to name a few. As noted above, the system 105 may specifically omit this aspect in order to determine whether or not sufficient confidence can be obtained without it.

According to the present technology, the system 105 may ensure that the methods described herein can be performed in a timely manner. For example, with regard to single requests, it may be desirable for the response time for a single request to be rapid, to avoid latency and delays in presenting the suggested classifications to the user. When multiple requests are involved, the system 105 may implement the methods within a Software as a Service (SaaS) environment. It may be desirable for the response time to remain consistent (e.g., not degrade) under concurrent usage. As a mitigating factor, because there may be no write component used by the system 105 in some embodiments, this may be a highly parallelizable process.

The system 105 may be configured to provide additional classification features such as cross checking of classified text with existing classifications, such as when event text has been manually classified by an individual. The system 105 may obtain a random sampling of events and reclassify them with the classification method. The system 105 may then compare the computed result with the manual classification. This cross check process may yield a probability of correct classification that can be used to determine accuracy. For example, the system 105 may determine that an event has been correctly classified 75% of the time.

The system 105 may also selectively vary parameters and recheck classifications using an initial cross check as a base line for determining whether each variation results in an improvement in accuracy. Potential variations include: (a) correlation of Event Type, Nature, and Sub-Nature; (b) correlation of tokens within the narrative text. For example, token a+b taken together make a given classification more likely than either of them would separately; (c) token equivalence; (d) geographical location. For example, the system 105 may consider only events in a similar location, such as a city or a particular hospital or physicians group; (e) care setting; and (f) department.

The system 105 may also obtain a random sampling of events from a distribution ordered by narrative text length and determine the average response time for the classification method. It will be understood that this process may yield an average expected response time for a single classification (assuming similar environments).

In some embodiments, the system 105 may obtain a random sampling of events from a distribution ordered by narrative text length and determine the average response time under concurrent loads of 5, 10, and 100 concurrent requests. This function may yield an average expected impact of response time on classification requests under various loads.

Given the result of these steps, the system 105 may provide sufficient information to determine a confidence level in the approach, informing the decision to implement a full production solution to the classification problem using the proposed direction.

In a more specific example, the system 105 may implement the classification of events by first measuring an initial baseline confidence. This confidence may provide a yardstick to measure the impact of variations in the inference method. Using empirical test data, the system 105 was used to classify various events. Analysis of these events reveals that there may, for example, be 3,410,405 events, of which 3,331,484 have a narrative text associated. Of these, 128,009 events may be classified as "Other" (Event Type 10000, 20000, or 30000). The average number of characters per event may be 313.77, with a median of 232, and a mode of seven.

To measure the initial baseline, the system may generate of tokens using a simple one word=one token tokenizer. In addition, the tokenizer of the system 105 ignores all digits and punctuation marks, and only considers words of at least two characters. Running this tokenizer resulted in 121,703, 504 tokens, with an estimated additional storage requirement of around 2 GB. The minimum number of tokens on any event may be one, and the maximum number of tokens may be 356. The average number of tokens per event may be 36.53, with a median of 30, and a mode of 18.

Next, the system 105 may compute baseline statistics for each token that was generated from the source input text regarding the event. For example, the system 105 may calculate a probability Pt that a given token indicates a trait t using Equation One below:

$$P_t = \frac{N_t/N_e}{N_t/N_e + M_t/M_e} \quad (1)$$

This probability $P_t$ is calculated by dividing a number of occurrences $N_t$ of a given token on events of trait t by a number of events $N_e$ of trait t. This resultant value is divided by a sum of the number of occurrences $N_t$ of a given token on events of trait t divided by the number of events $N_e$ of trait t, plus a number of occurrences $M_n$ of a given token on events not of trait t, divided by a number of events $M_e$ not of trait t.

The system 105 may perform this calculation in approximately 27 for all tokens minutes in some embodiments, and may result in 11,603,336 rows in a TokenStatistic table. An example of a TokenStatistics table is provided below with reference to Table 1.

TABLE 1

| Token | DimensionId | TraitId | TraitValueId | Probability |
|---|---|---|---|---|
| arteriogram | 0 | 4 | 1 | 0.805449708 |
| arteriogram | 0 | 4 | 3 | 0.678337633 |
| arteriogram | 0 | 4 | 4 | 0.606263856 |
| arteriogram | 0 | 4 | 5 | 0.409886078 |
| arteriogram | 0 | 4 | 7 | 0.892424925 |
| arteriogram | 0 | 4 | 10 | 0.698047061 |
| arteriogram | 0 | 4 | 16 | 0.733080198 |
| arteriogram | 0 | 4 | 17 | 0.887128607 |
| arteriogram | 0 | 4 | 18 | 0.67056038 |
| arteriogram | 0 | 4 | 26 | 0.919348981 |
| patient | 0 | 4 | 1 | 0.520203101 |
| patient | 0 | 4 | 2 | 0.518718792 |
| patient | 0 | 4 | 3 | 0.501818848 |
| patient | 0 | 4 | 4 | 0.519043205 |
| patient | 0 | 4 | 5 | 0.410455793 |
| patient | 0 | 4 | 6 | 0.509020932 |
| patient | 0 | 4 | 7 | 0.51874027 |
| patient | 0 | 4 | 8 | 0.431160994 |
| patient | 0 | 4 | 9 | 0.518718633 |
| patient | 0 | 4 | 10 | 0.519286519 |

Two example tokens are shown in the example above: "arteriogram" and "patient." DimensionId may correspond to different dimensions related to the token. For example, for the patient token, these dimensions may be the department associated with the patient, a time the event was reported for the patient, or the age of the patient. The TraitID column may indicate the levels of classification the token will be classified in. For example, a "4" indicates that the token will be classified to event, type, nature, and subnature. In some embodiments, up to six levels of classification may be used. Fewer classifications may also be used in various embodiments. The TraitValueId column may correspond to the identity of a taxonomy item which may potentially be associated with the token. A classification table linked the token statistics table may include a mapping of a taxonomy item with the number in the TraitValueId column. For example, taxonomy item 1 may be associated with a misreading of diagnostic information, while taxonomy item 5 may be associated with using an incorrect amount of contrast material in a diagnostic test.

Finally, the probability column may include a value between 0 and 1 that indicates conditional probability that the event is classified to the taxonomy item (indicated by the TraitValueId column) when a narrative includes the token in question. The probability value may indicate how strongly a token is related to the taxonomy item in question. In the example shown above, the token "arteriogram" may have higher probabilities than the "patient" token, because "arteriogram" has greater descriptive value as to the nature of the events indicated by the taxonomy items.

Next, the system 105 further determines the baseline confidence by building basic inference logic, using the following exemplary Equation Two:

$$P_t = \frac{\Pi P_k}{\Pi P_k + \Pi(1 - P_k)} \quad (2)$$

In the exemplary equation, $P_t$ is a probability that trait t is a correct classification for the event, and $P_k$ is a probability that token k indicates trait t. The system 105 may compute a set of tokens involved in the narrative text for the event. Using Equation Two, the system 105 may combine the probabilities associated with each token in the event into a probability for each trait, and return the n most likely traits.

Figure 2:
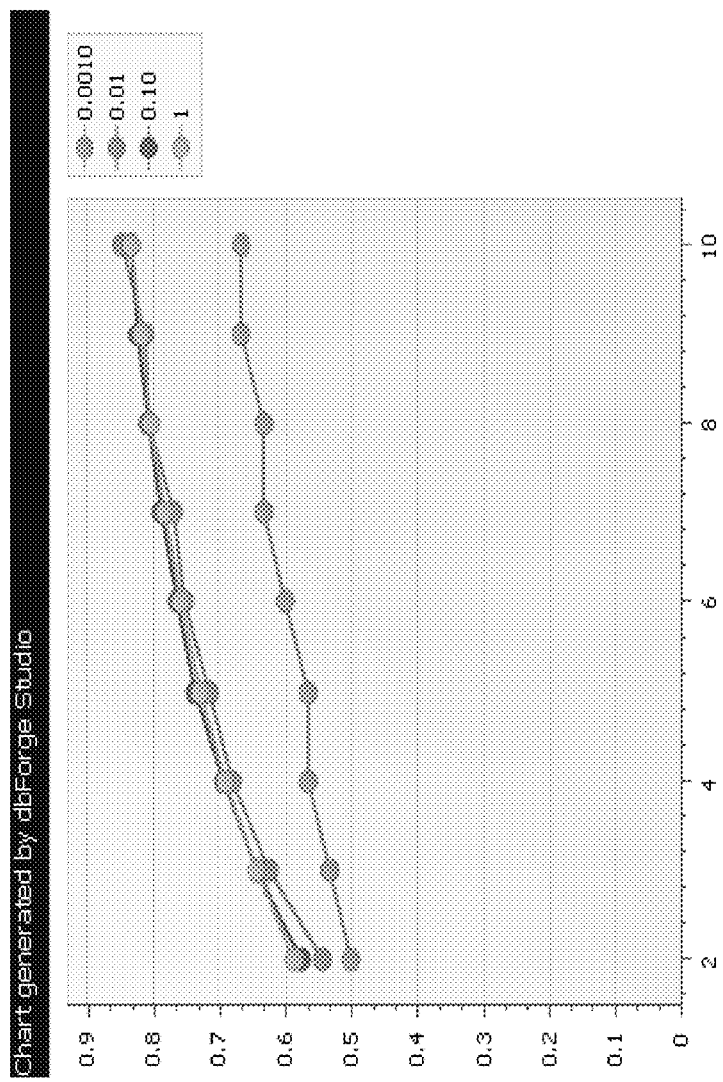
FIG. 2 is an exemplary graph that illustrates the output of the calculations by the system of FIG. 1.

With the inference mechanism established, baseline confidence may be measured by the system 105 by taking a random sampling of events and computing the most likely suggested traits for each event. The suggested traits may then be compared against the actual traits for each event to determine a percentage accuracy, or confidence. For example, to determine the optimal sample size, this confidence may be measured for n from 2 through 10 for Event Type only, with sample sizes of 0.001%, 0.01%, 0.1%, and 1.0%. FIG. 2 is an exemplary graph 200 that illustrates the output of the calculations by the system 105. Confidence levels are displayed on the vertical axis, while the n most likely traits are displayed on the horizontal axis. The sample sizes are placed onto the graph and are linked using lines.

The sample size of 0.001% may be too small to give accurate results, but there may be no significant difference between the results for sample sizes of 0.01%, 0.1%, and 1%. As a result, confidence measurements may all be taken at the 0.01% sample size.

The following descriptions of graphs (FIGS. 2-25) generated by the system 105 are illustrative of the output of the various calculations described above. These graphs reflect internal operations of the system 105 and are provided for contextual purposes. The system 105, while being able to output various graphs, does not require the generation of graphs or other output to perform the classification methods described herein.

Figure 3:
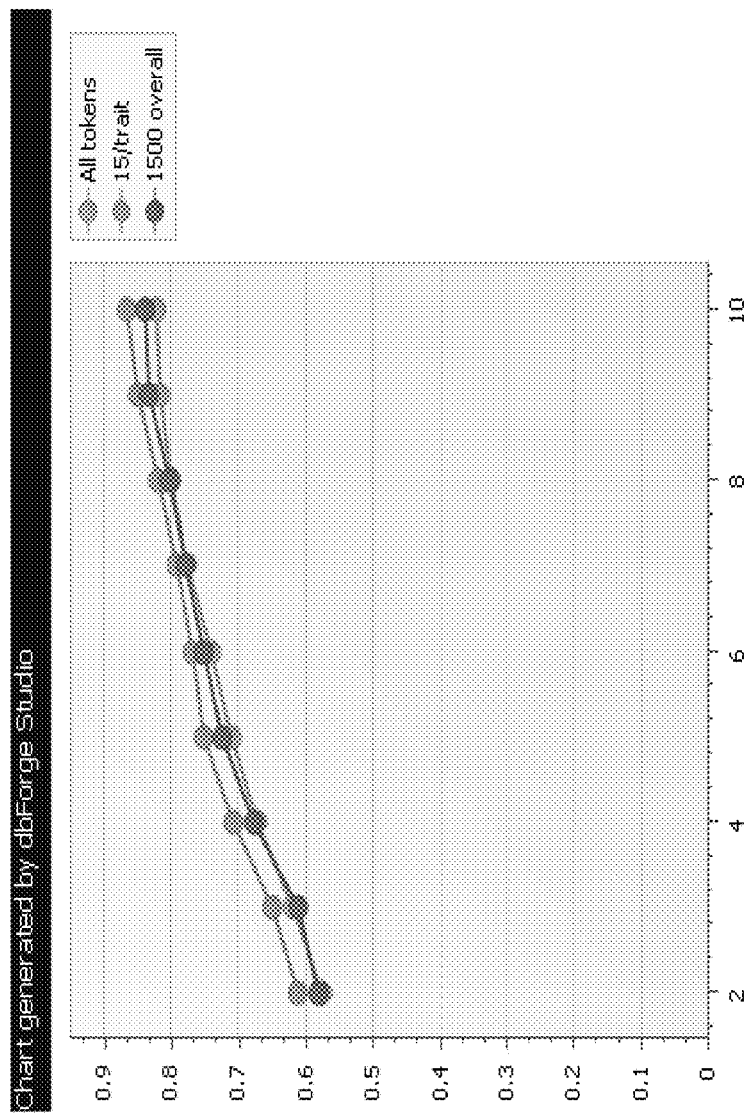
FIG. 3 is a graph that illustrates the impact of varying the number of "interesting" tokens used in an inference calculation.

FIG. 3 is a graph 300 that illustrates the impact of varying the number of "interesting" tokens used in the inference. The system 105 may consider all tokens; may consider only the 15 most interesting tokens per trait; or may consider 1500 (15 tokens*10 suggestions) interesting tokens, regardless of trait, in various embodiments.

The use of "interesting" tokens, as opposed to all tokens may improve the confidence, which may significantly improve performance by reducing the number of tokens considered per trait, rather than having to combine all possible probabilities for all possible traits.

Figure 4:
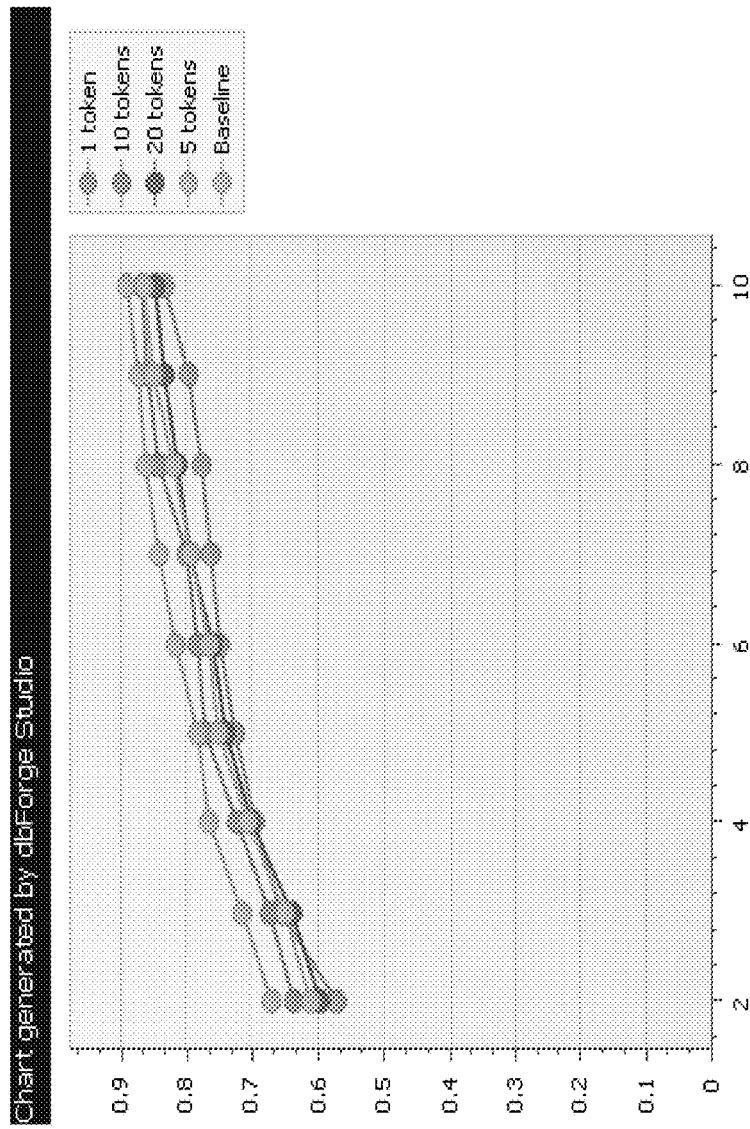
FIG. 4 is a graph that illustrates only the five most interesting tokens per trait that resulted in the best confidence values.

FIG. 4 is a graph 400 that illustrates the determination of an optimal number of interesting tokens per trait. FIG. 4 illustrates the impact of a change in confidence on this value. Considering only the five most interesting tokens per trait resulted in the best confidence values.

Figure 5:
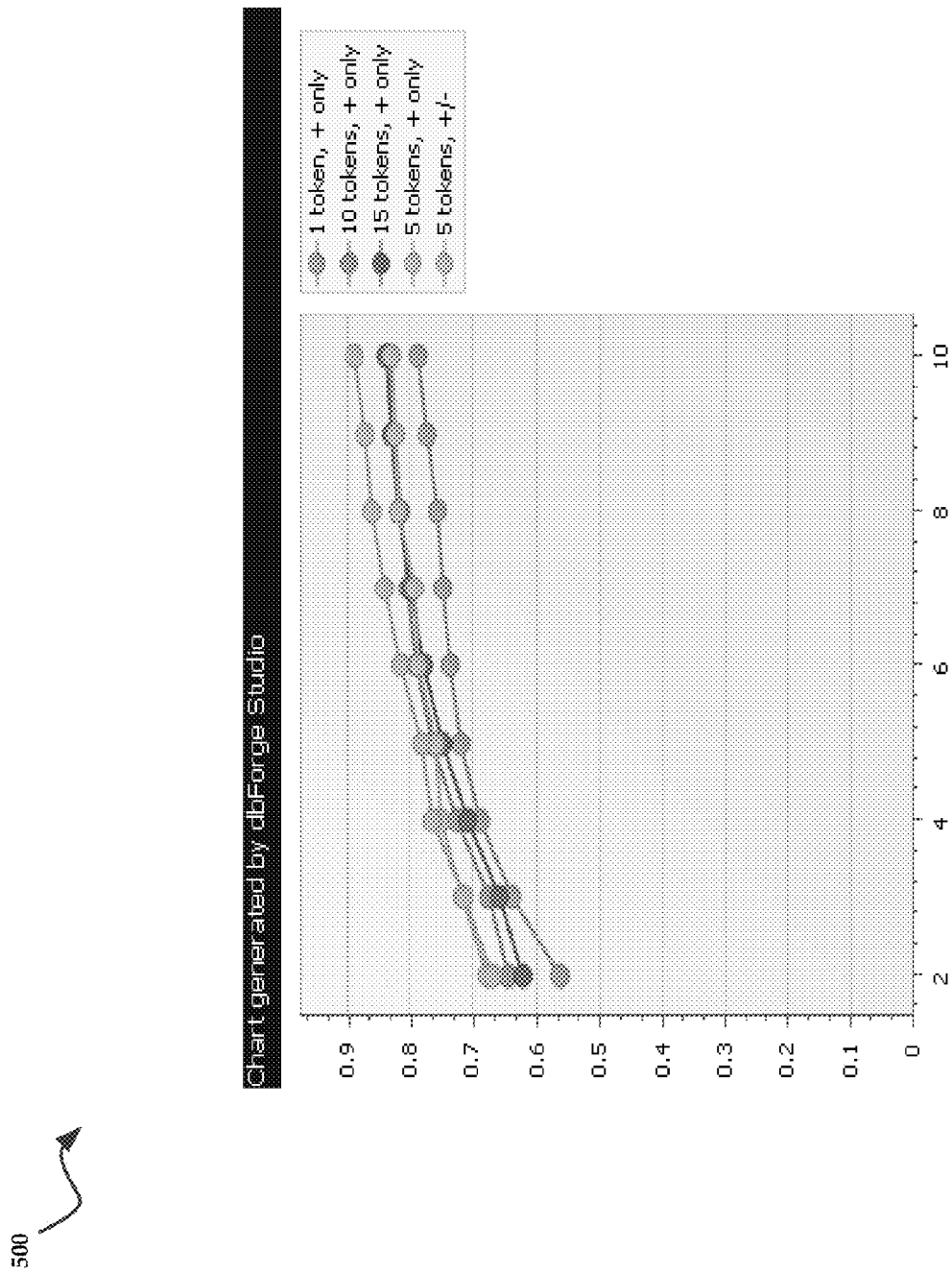
FIG. 5 is a graph that illustrates another test of number of tokens amounts.
Figure 6:
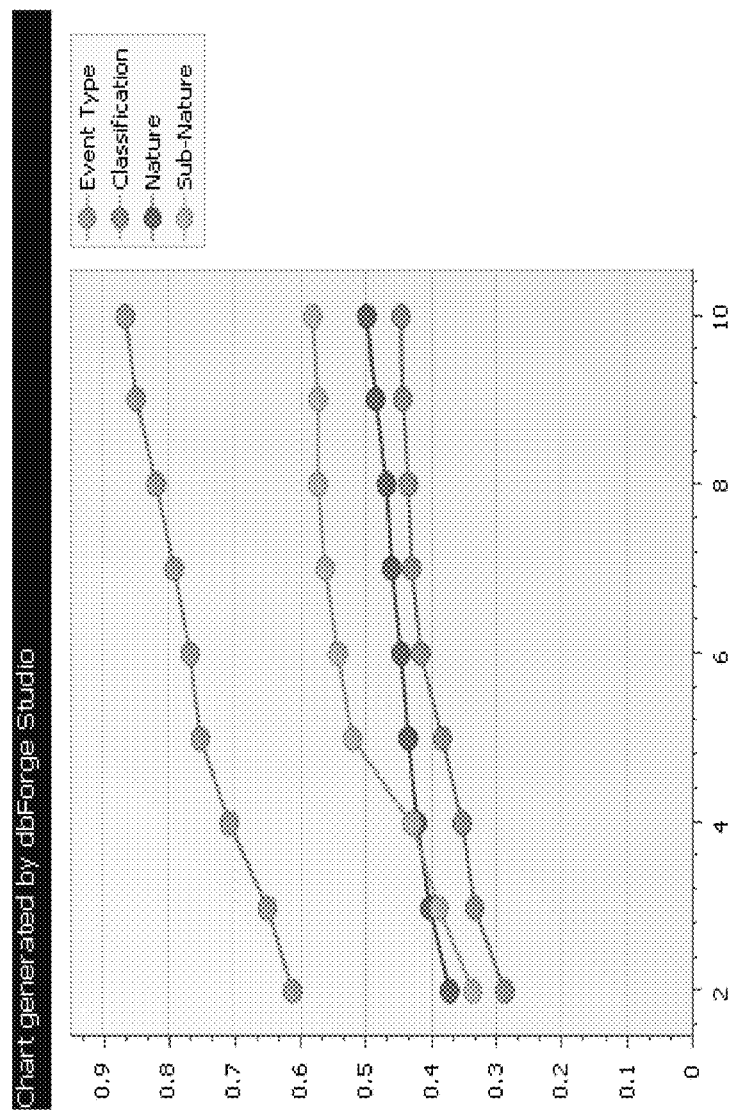
FIG. 6 is a graph that illustrates the establishment of baseline confidence measurements.

FIG. 5 is a graph 500 that illustrates another test of number of tokens. A variation may be tested to include only the positive probabilities for each trait n. It will be understood that considering only positive probabilities may result in equivalent for low suggestion counts, but overall, considering both positive and negative probabilities may result in better confidence. FIG. 6 is a graph 600 that illustrates the establishment of baseline confidence measurements.

With the basic methodology in place and baseline confidence established, the system 105 may employ several statistics variations and determine their impact on various aspects of the classification methodology.

For example, the following scenarios may be measured for each statistics variation, considering positive and/or negative probabilities: (1) the five most interesting tokens (positive and negative); (2) the ten most interesting tokens (positive and negative); (3) the 15 most interesting tokens (positive and negative); (4) the five most interesting tokens (positive only); (5) the ten most interesting tokens (positive only); and (6) the 15 most interesting tokens (positive only). These variations are merely exemplary and may be adjusted as desired. These variations are plotted in graphs 600-800 of FIGS. 7-9, respectively.

Figure 7:
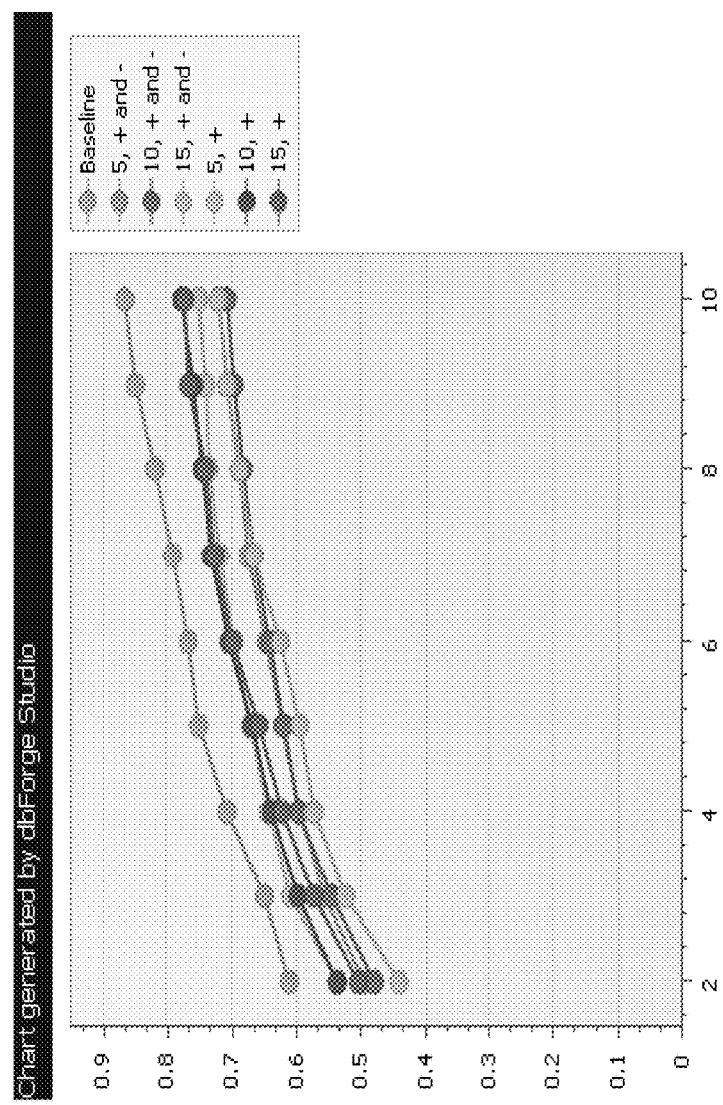
FIG. 7 is a graph that illustrates the computation of statistics only for tokens that appeared on events that occurred within the most recent month of activity.
Figure 8:
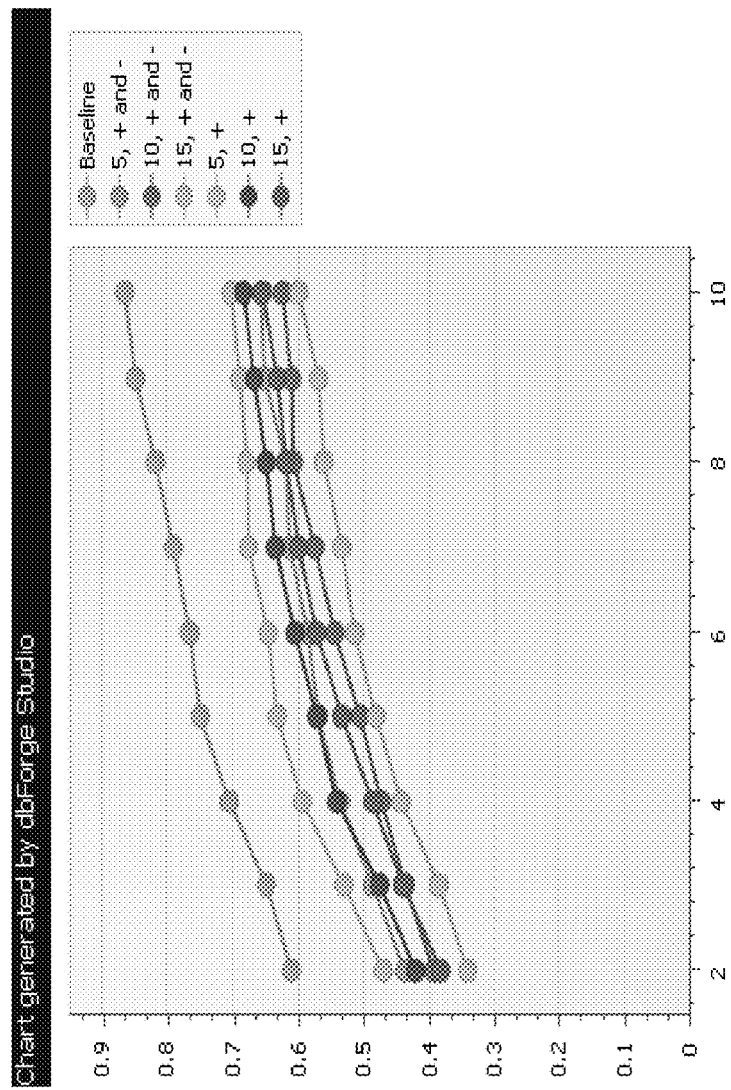
FIG. 8 is a graph that illustrates statistics which are computed only for tokens that appeared on the most recent 10 events per trait value.
Figure 9:
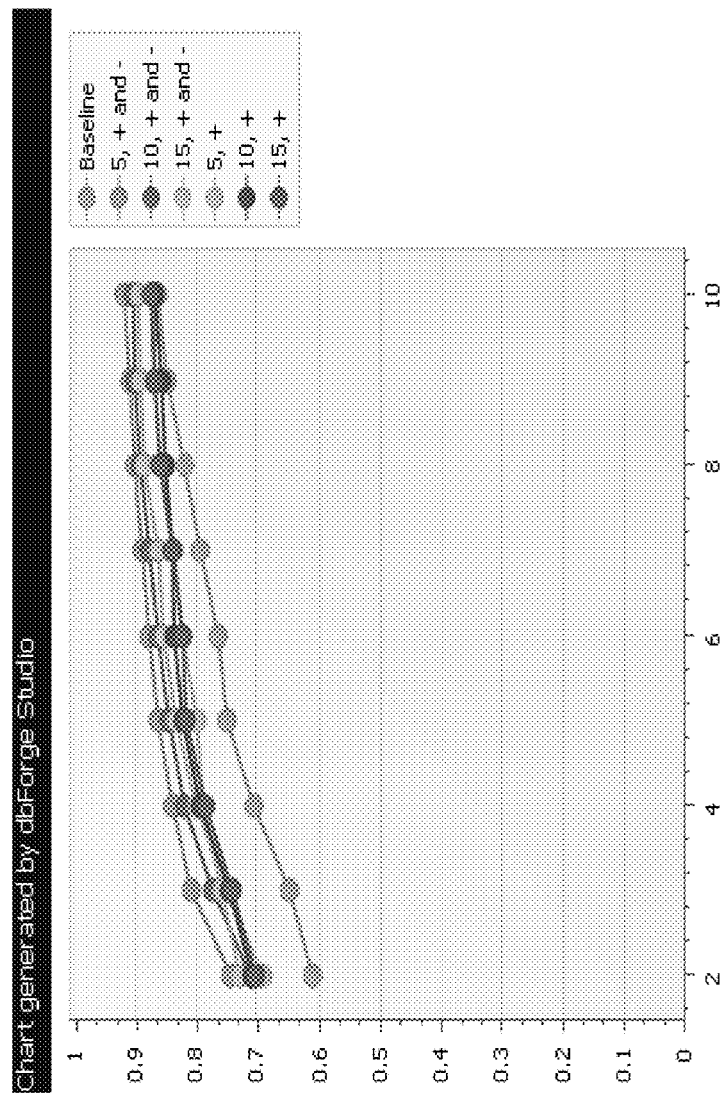
FIG. 9 is a graph that illustrates statistics which may be computed only for trait values that had at least n events per trait, where n=5000.

FIG. 7 is a graph 700 that illustrates the computation of statistics only for tokens that appeared on events that occurred within the most recent month of activity. FIG. 8 is a graph 800 that illustrates statistics which are computed only for tokens that appeared on the most recent ten events per trait value. FIG. 9 is a graph 900 that illustrates statistics which may be computed only for trait values that had at least n events per trait, where n=5000.

Figure 10:
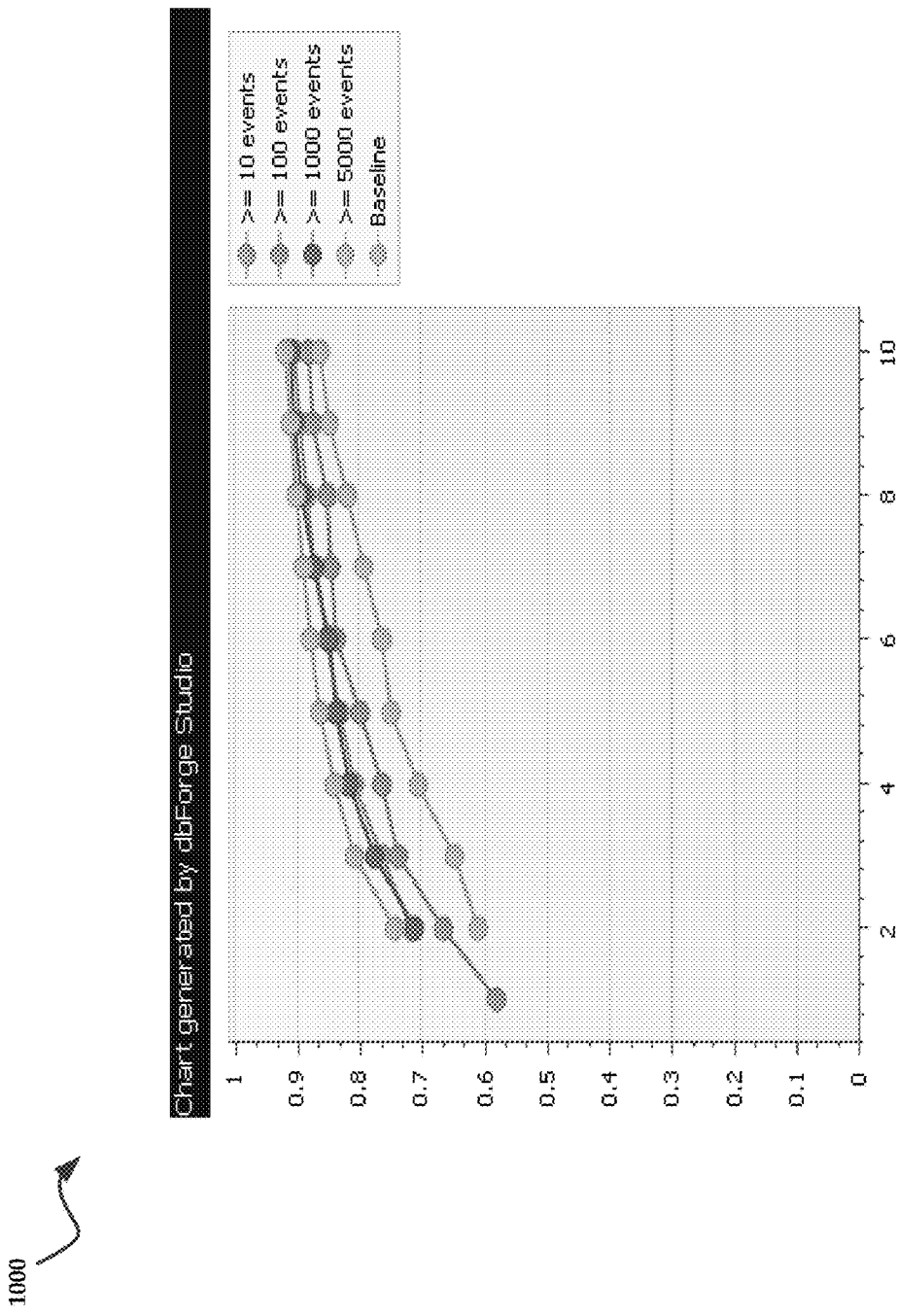
FIG. 10 is a graph that illustrates results generated by the system of FIG. 1 when combining the results for various values of n, for the event type trait.

FIG. 10 is a graph 1000 that illustrates results generated by the system 105 when combining the results for various values of n, for the event type trait.

The system 105 may be configured to determine other statistical variations such as biases. The system 105 may bias token probabilities based on various factors. For example, the system 105 may consider biasing probabilities towards, and away, from classification. This may be done when the system computes 105 a probability for a specific trait by counting token occurrences twice when the token appears on an event for that trait. The opposite scenario may also be tested, by counting non-token traits twice.

Figure 11:
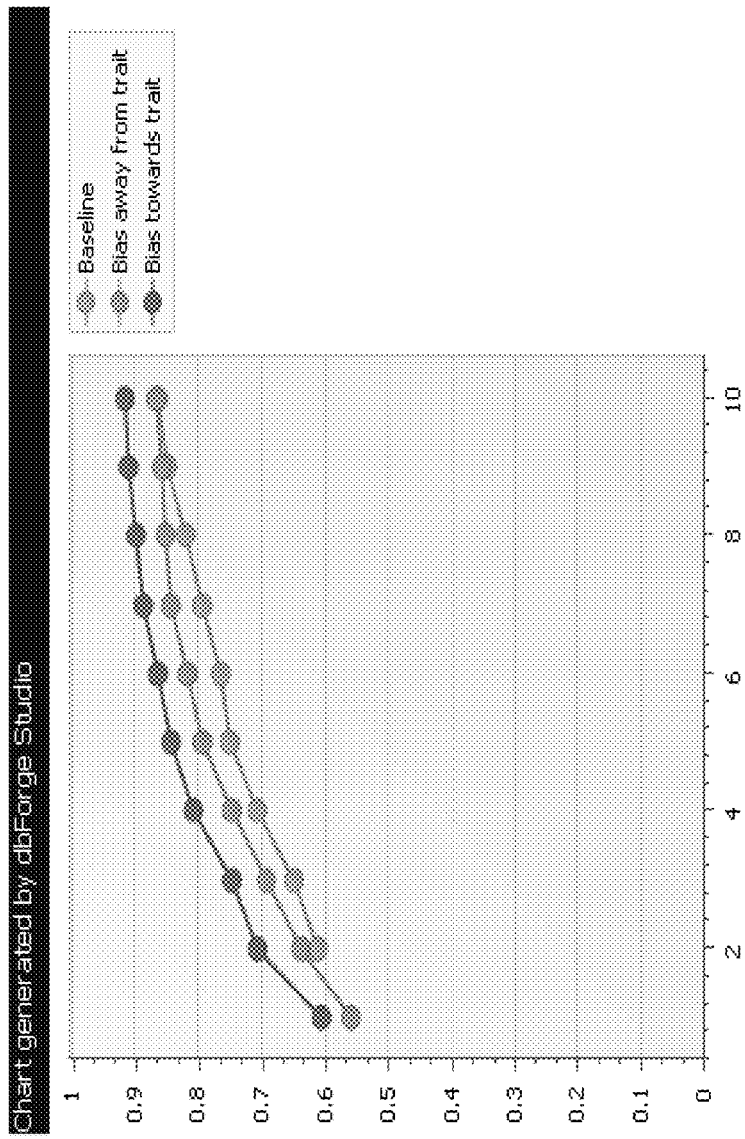
FIG. 11 is a graph that illustrates that depicts the output of the system FIG. 1 biasing towards traits.
Figure 12:
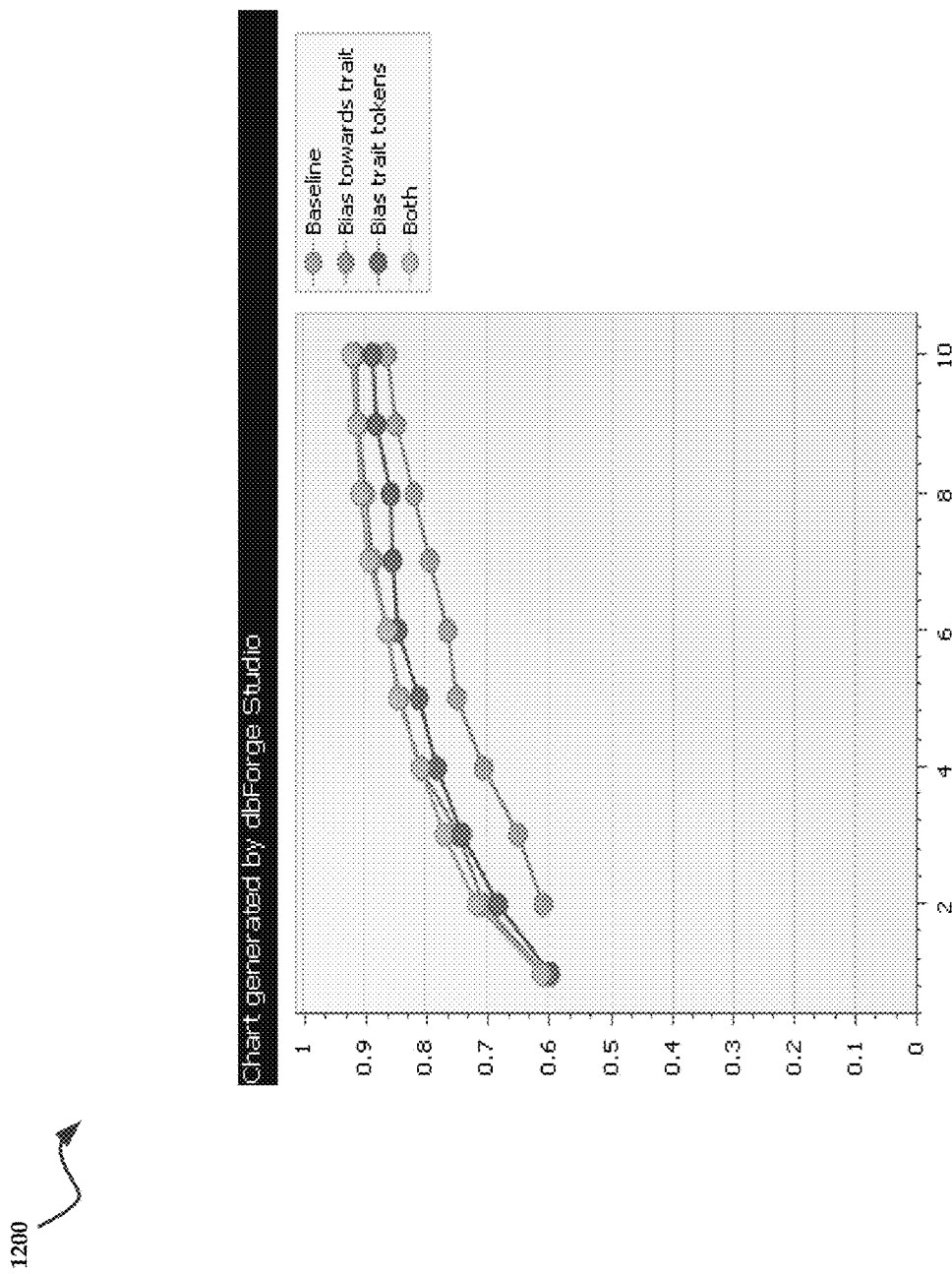
FIG. 12 is a graph that illustrates medical terms that were biased using two different medical dictionaries, plotting a first and second terms lists.

FIG. 11 is a graph 1100 that illustrates that depicts the output of the system 105 biasing towards traits. Next, the system 105 biases trait tokens, meaning that any token that appears in the description of a trait may be given extra weight for that trait probability, as shown in the graph of FIG. 12.

Figure 13:
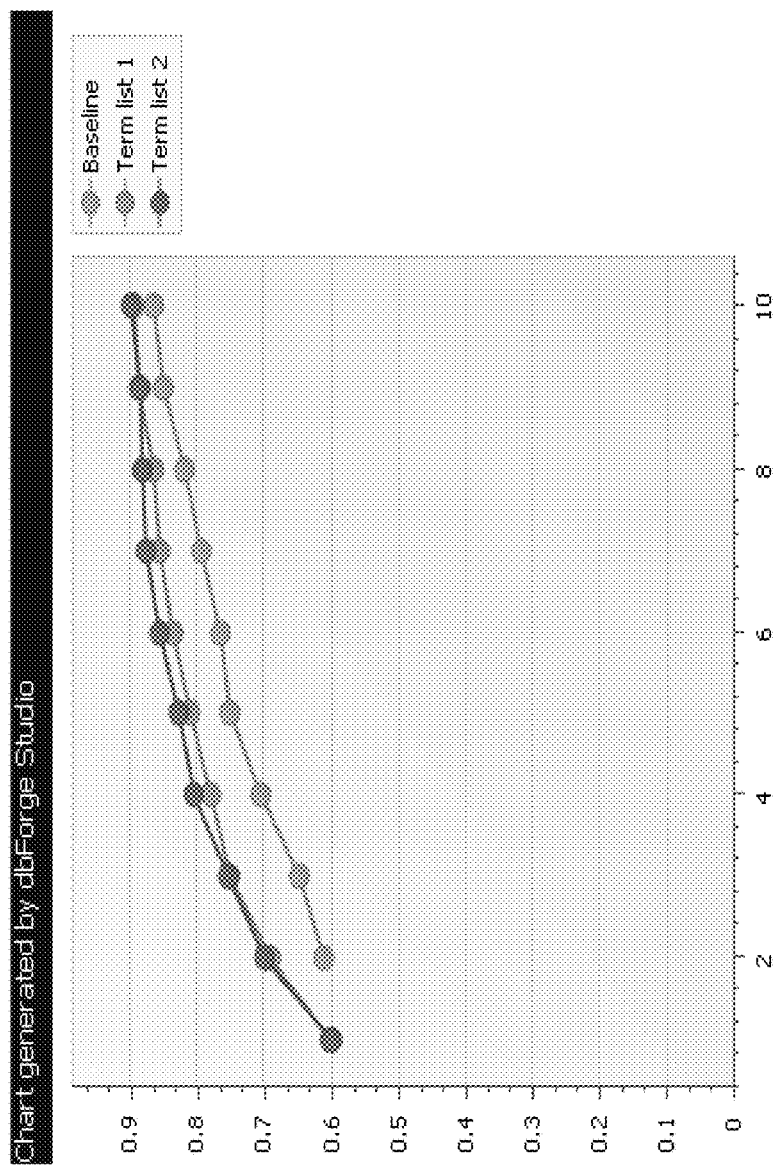
FIG. 13 is a graph that illustrates results for Event Type traits.

In a specific implementation in the medical field, the system 105 may be configured to bias, for example, medical terms using two different medical dictionaries. In the exemplary embodiment, any token that is also a medical term may be counted twice when computing probabilities. "Term list 1" displayed in graph 1200 of FIG. 12, may contain about 48,000 terms in the exemplary embodiment, and "Term List 2" may contain about 96,000 terms. FIG. 13 is a graph 1300 that illustrates for these event type traits.

Figure 14:
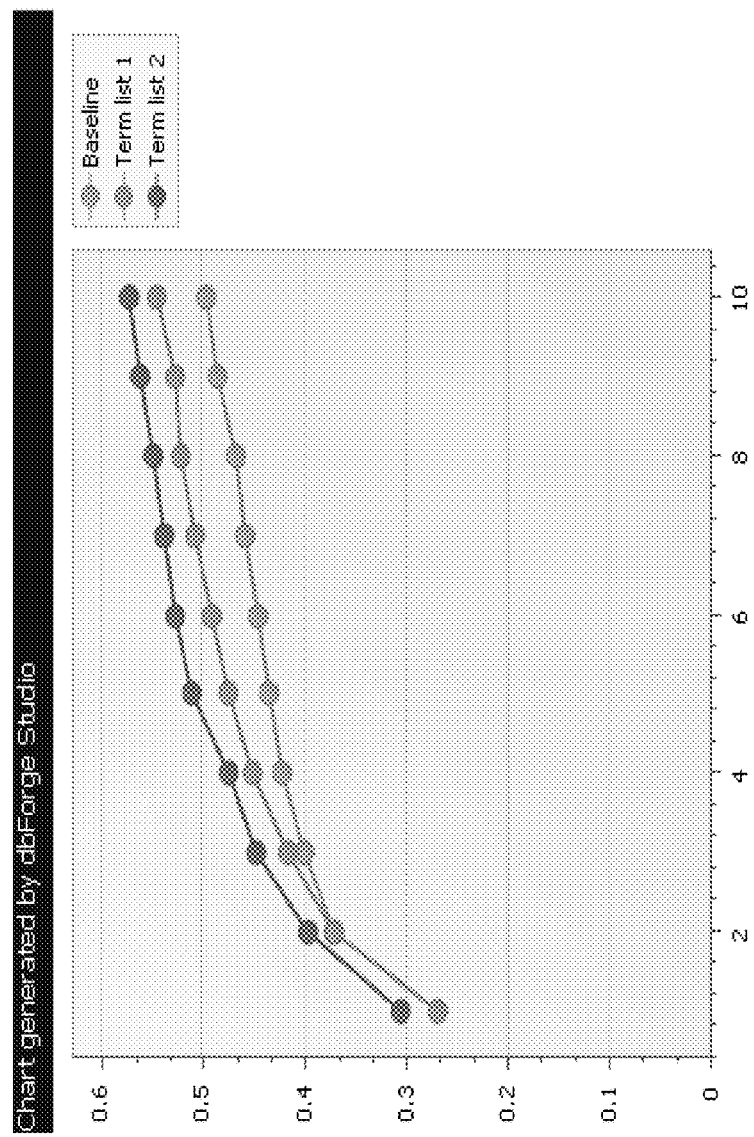
FIGS. 14 and 15 are graphs with respect to Natures and Sub-Natures, respectively.
Figure 15:
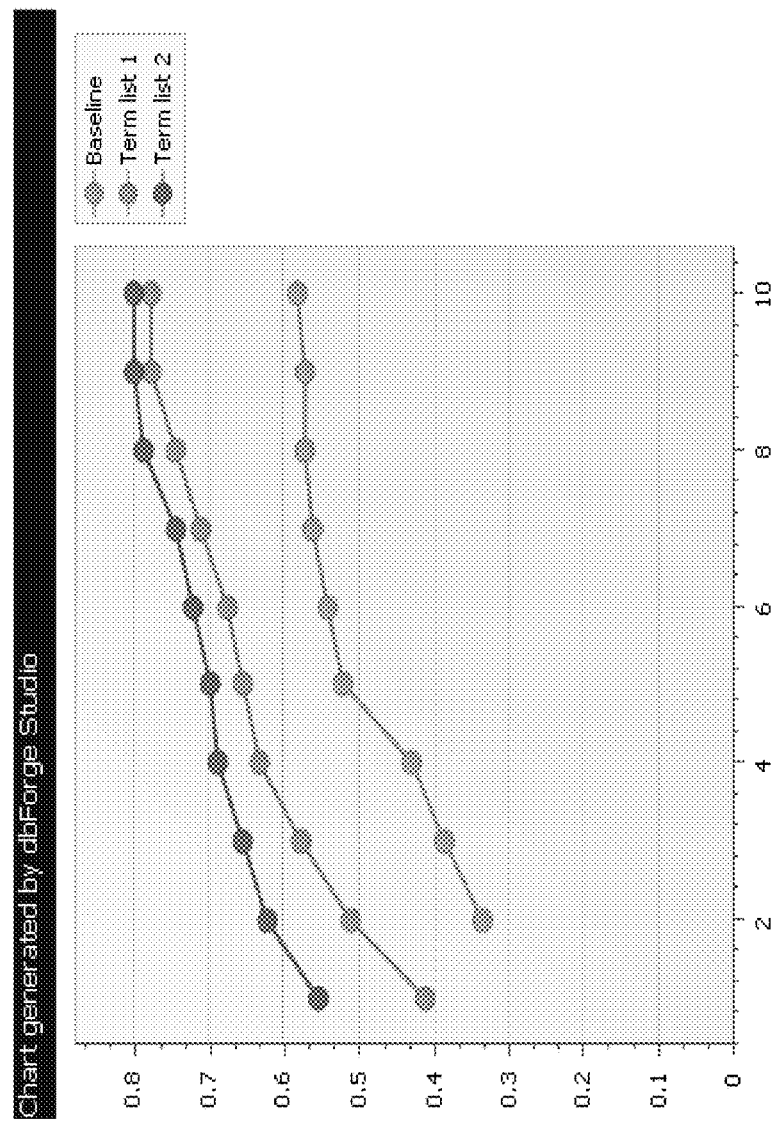
Figure 16:
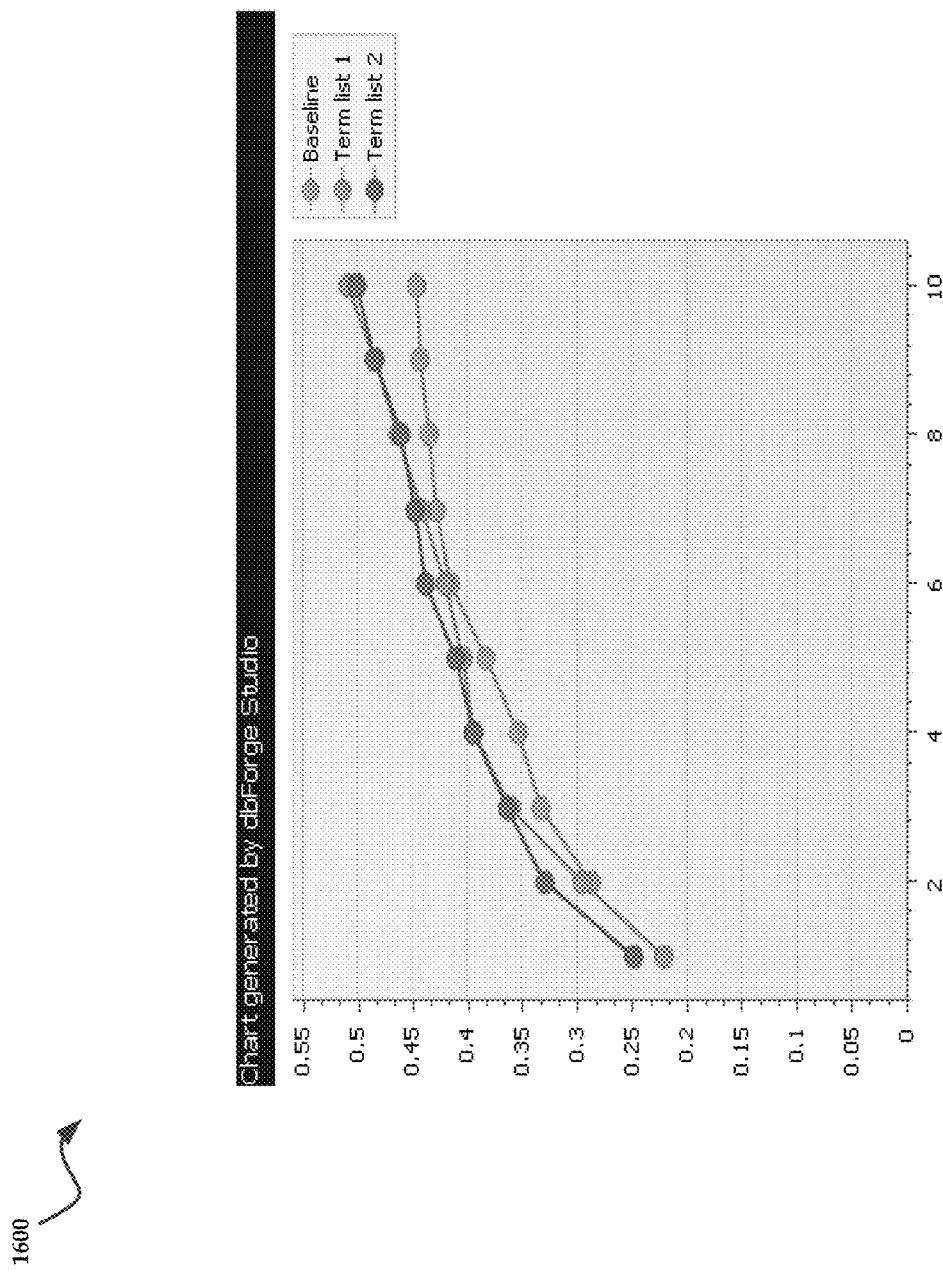
FIG. 16 is a graph that illustrates classification calculations.
Figure 17:
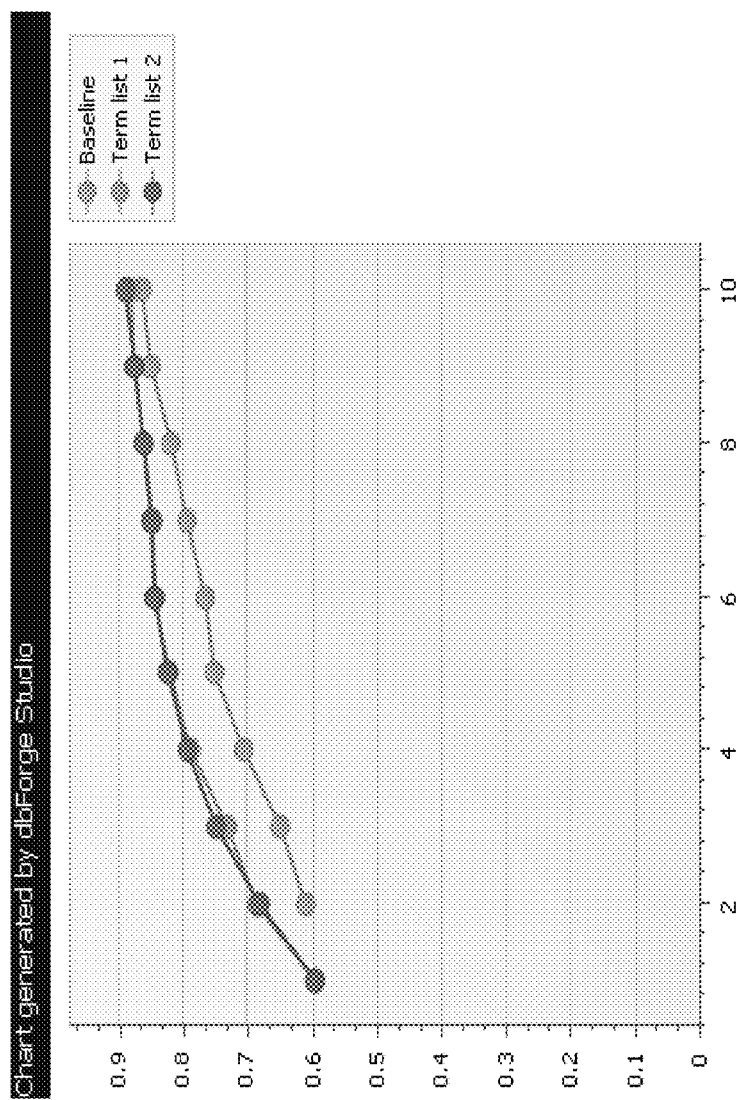
FIGS. 17-20 collectively illustrate the results for Event Type, Nature, Sub-Nature, and Classification using the two word lists of differing sizes.
Figure 18:
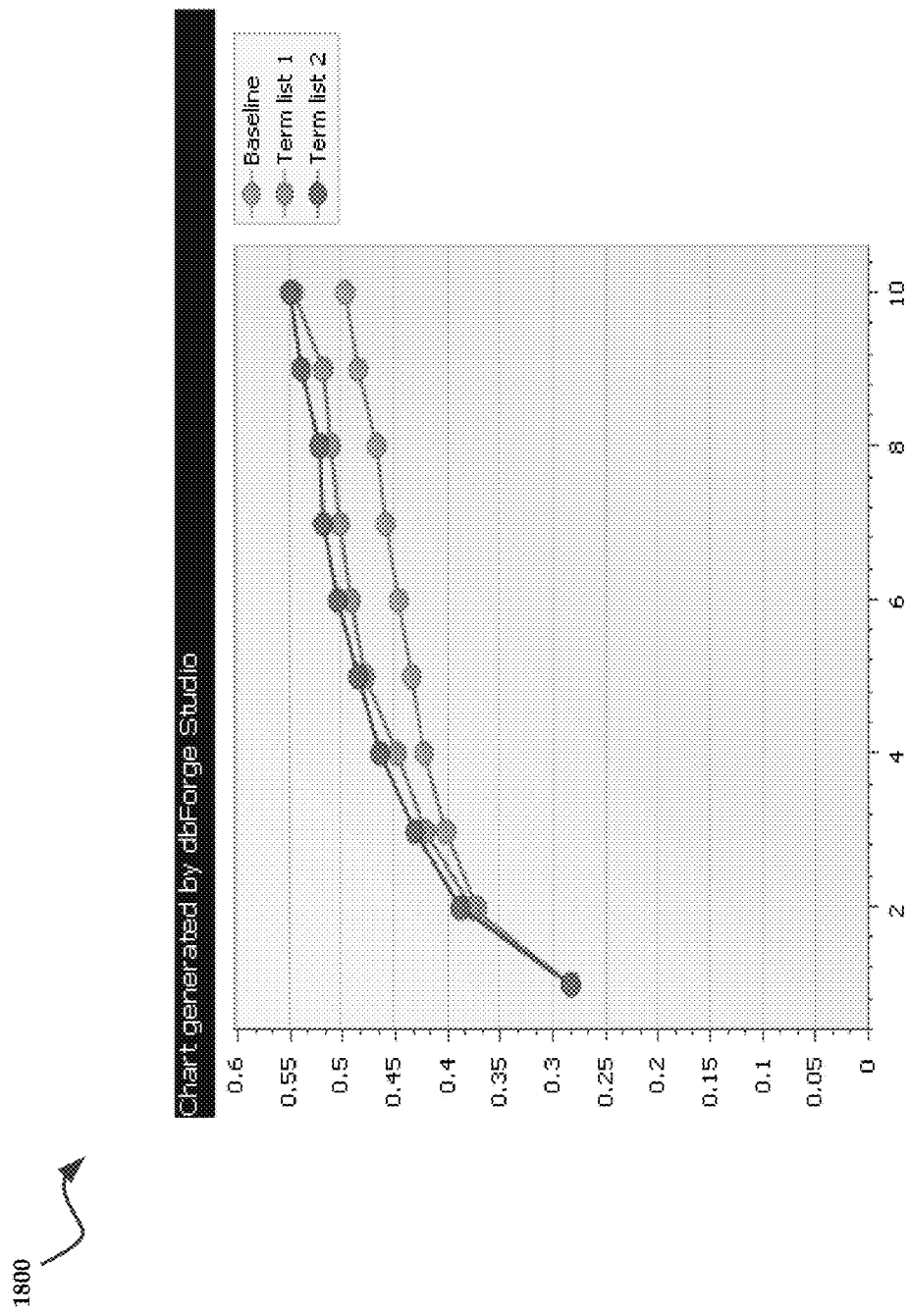
Figure 19:
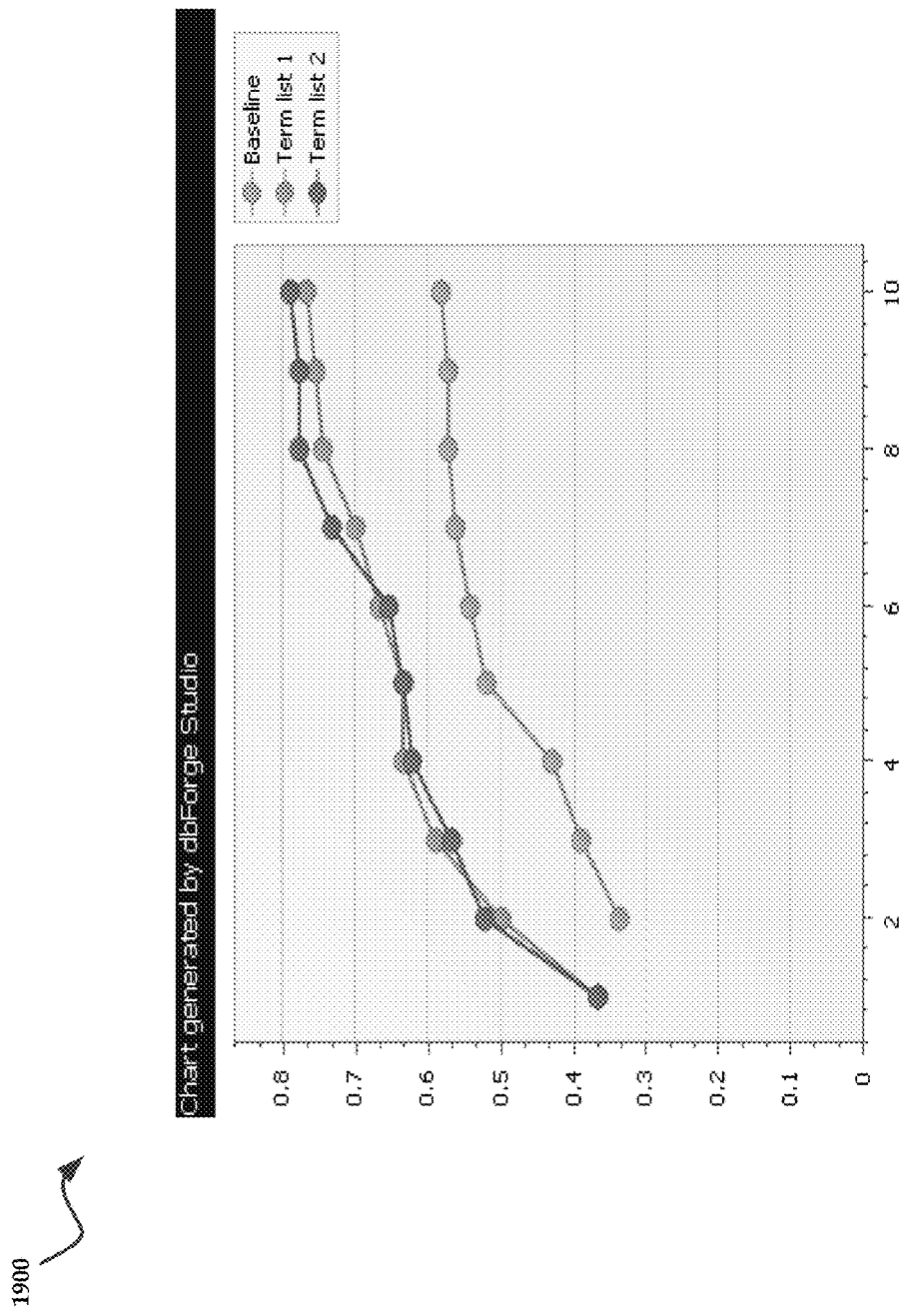
Figure 20:
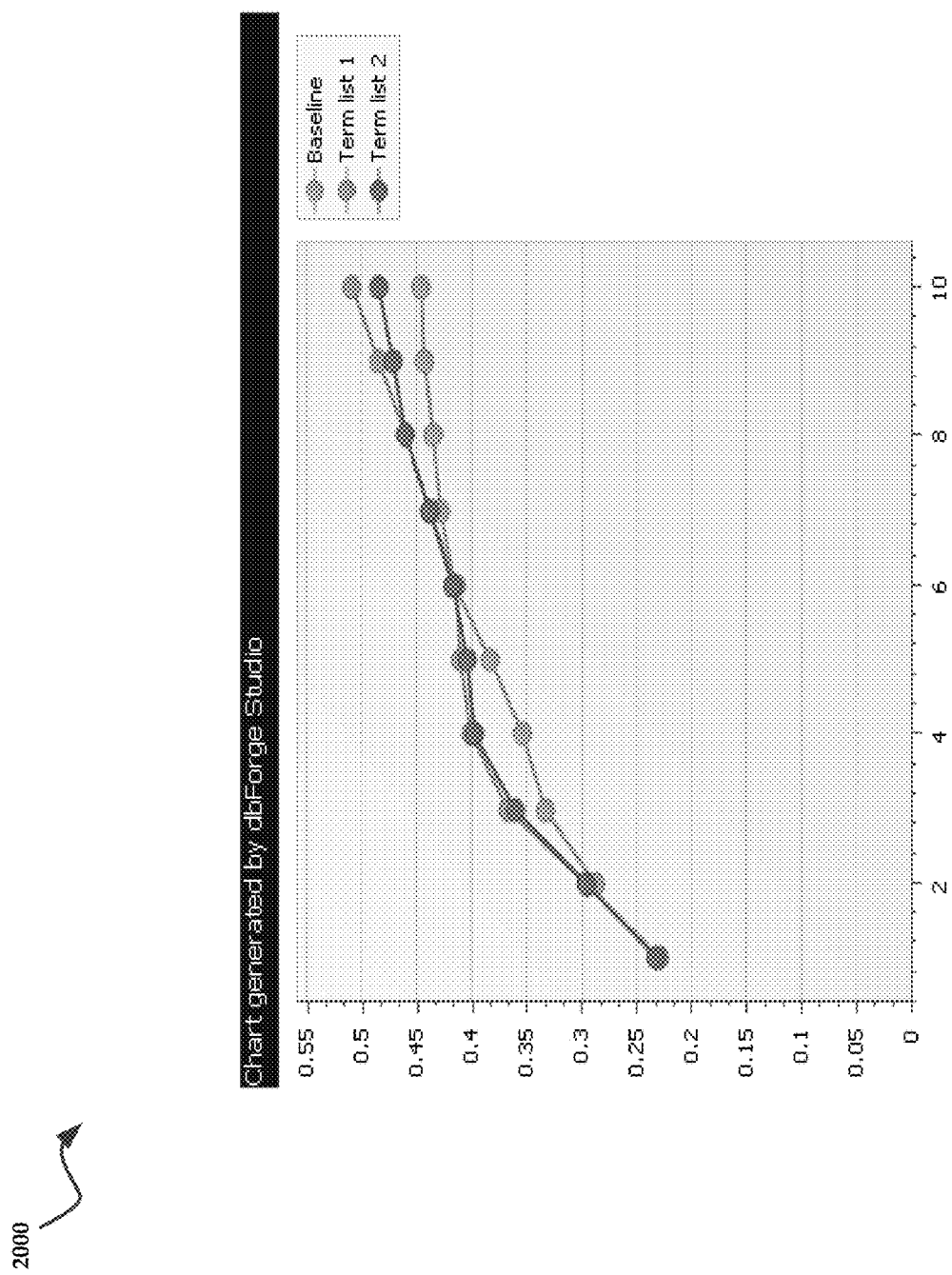

FIGS. 14 and 15 show graph 1400 and graph 1500 that are graphs with respect to Natures and Sub-Natures, respectively. Classifications are illustrated in graph 1600 of FIG. 16.

Correctly spelled terms may receive a bias using two different word lists. The first word list may have around 37,000 words, and the second word list may have an additional 222,000 words. FIGS. 17-20 show graphs 1700, 1800, 1900, and 2000, respectively, that collectively illustrate the results for Event Type, Nature, Sub-Nature, and Classification using the two word lists of differing sizes.

The system 105 may also be configured to vary the tokenization of event text in order to investigate confidence for the tokenization that is employed. For example, the system 105 may tokenize events differently (e.g., the event text received from an individual).

Figure 21:
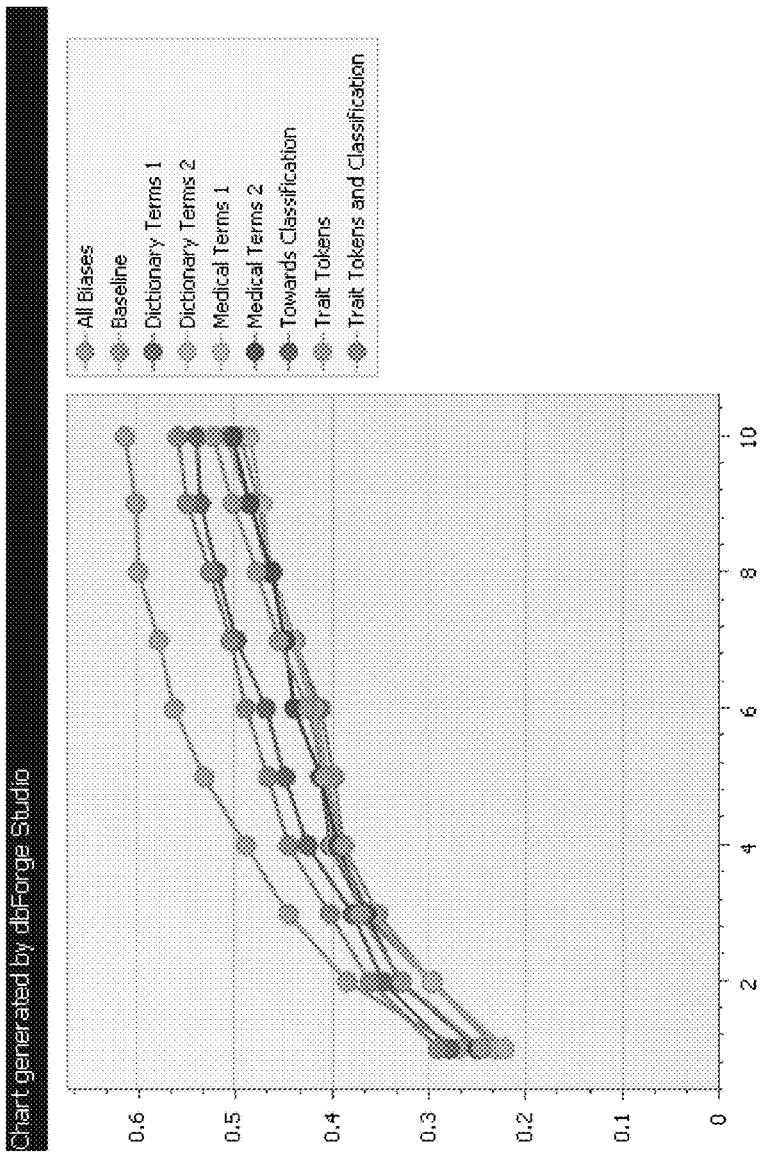
FIG. 21 is a graph that illustrates the effect of various biases on overall classification.

FIG. 21 is a graph 2100 that illustrates the effect of the various biases on overall classification.

Instead of each word mapping to a single token, tokens may be generated by considering each word, as well as each pair of words as a token. As with the simple tokenizer, digits and punctuation may be ignored, and word pairs may not be considered if separated by punctuation. For example, the following sentence "This is the description, or narrative, for an event." would be tokenized as follows in Table 2:

TABLE 2

| This | this is | Is | is the |
|---|---|---|---|
| The | the description | description | Or |
| or narrative | Narrative | For | for an |
| An | an event | | |

Figure 22:
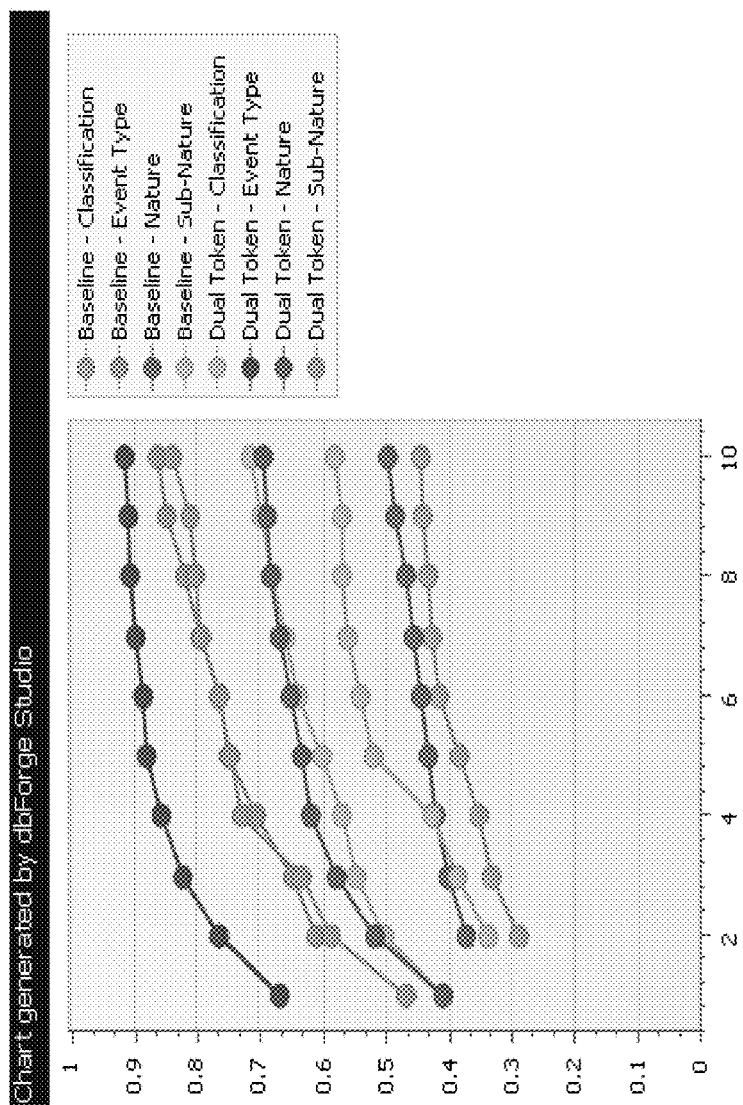
FIG. 22 is a graph that illustrates a contrast between baseline confidence measures against the dual token measurements for each trait.
Figure 23:
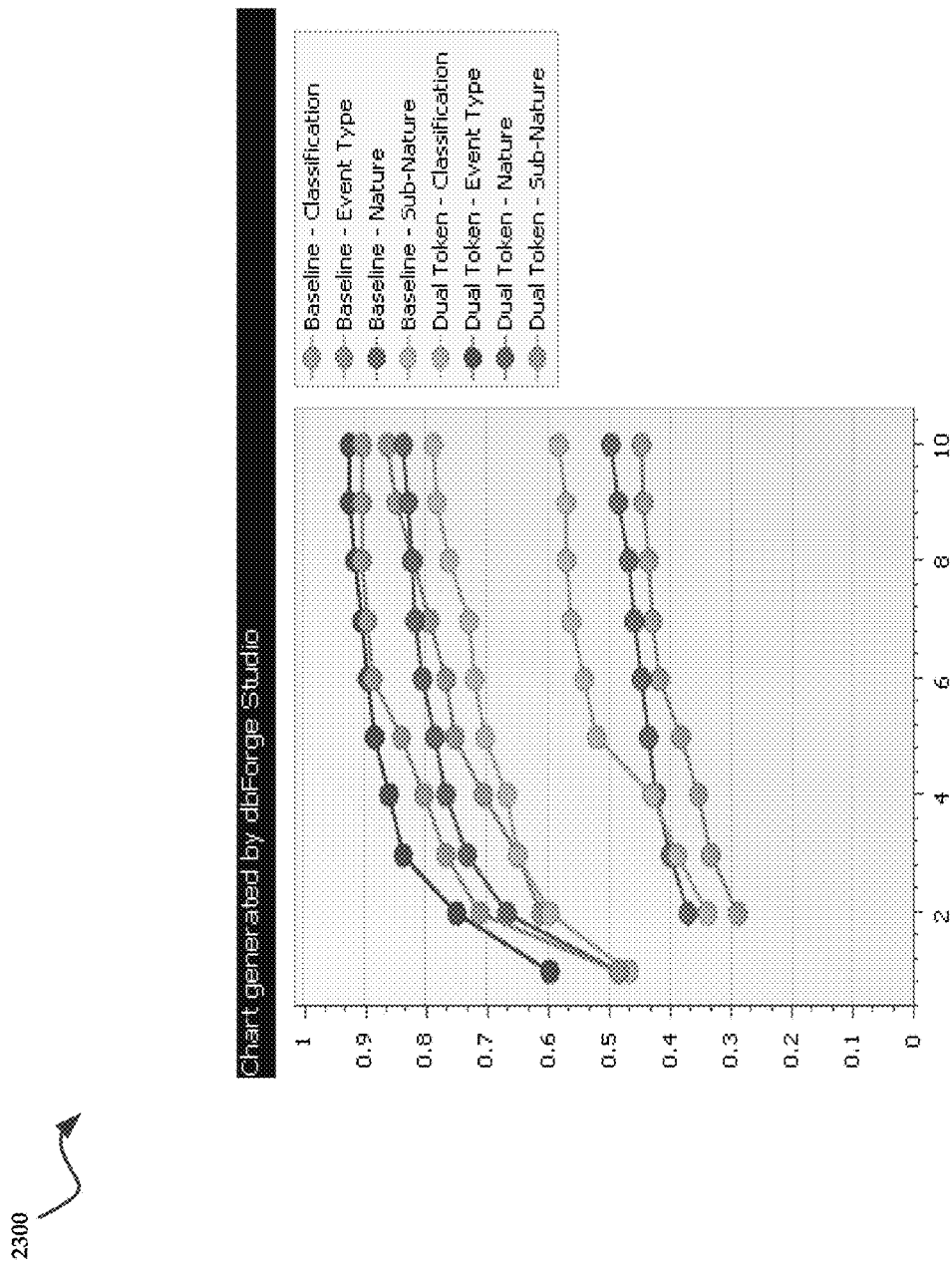
FIG. 23 is a graph that illustrates dual token measurements with a bias towards classification.

FIG. 22 is a graph 2200 that illustrates a contrast between baseline confidence measures against the dual token measurements for each trait. FIG. 23 is a graph 2300 that illustrates dual token measurements with a bias towards classification.

Figure 24:
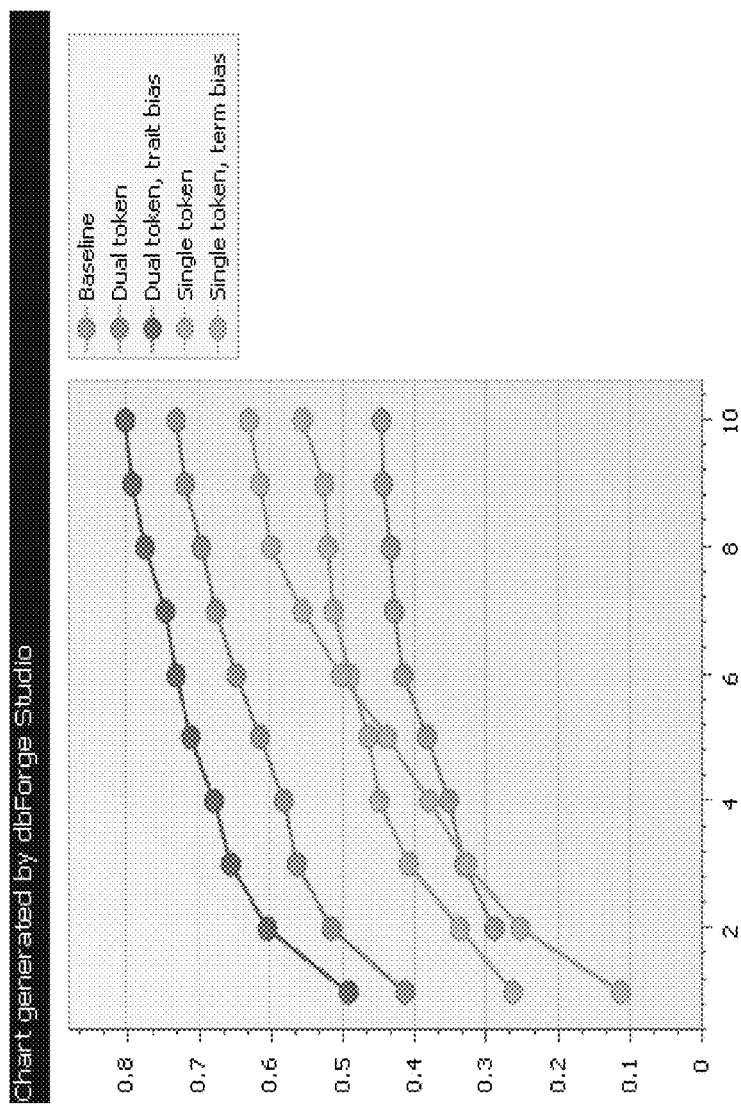
FIG. 24 is a graph that illustrates several of the best performing scenarios for overall classification with reasonableness filtering applied to filter the suggestions, as determined by the system of FIG. 1.

The system 105 may, in some instances, be configured to execute a reasonableness filtering scheme. Because statistics are computed by the system 105 over the set of all traits that have appeared on any event in the training corpus, the inference mechanism by default may produce suggested traits that may not be appropriate for the care setting and/or affected party type associated with the event. All the measurements detailed above in the exemplary embodiment do not take this into account. FIG. 24 is a graph 2400 that illustrates several of the best performing scenarios for overall classification with reasonableness filtering applied to filter the suggestions, as determined by the system 105.

The system 105 may also be configured to determine confidence within a given event type. To investigate the effectiveness of the inference for event types that have a large number of natures, the confidence within the five event types with the most natures, and the five event types with the least natures may be measured by the system 105.

Figure 25:
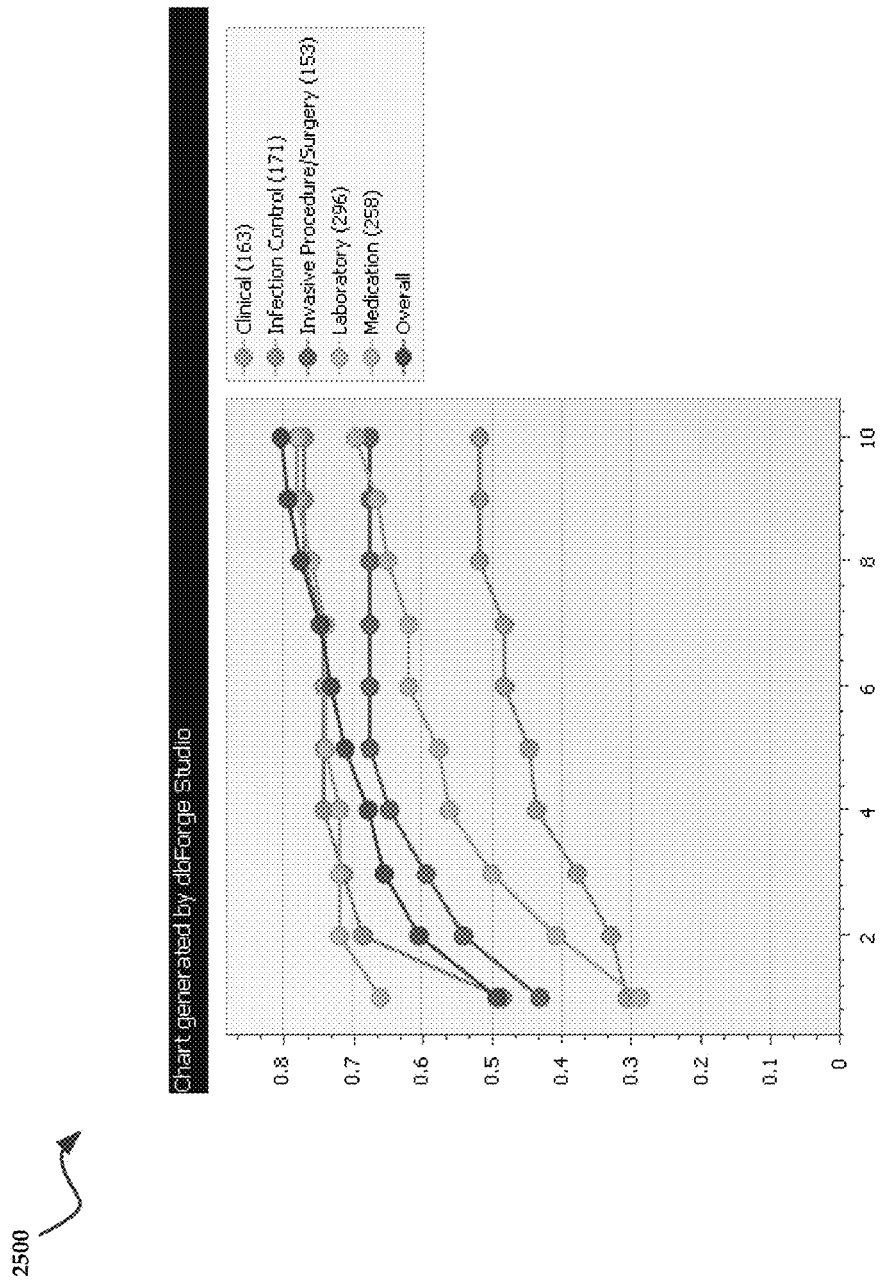
FIGS. 25 and 26 are graphs that collectively depict the confidence of classification within the five event types with the most natures (FIG. 25) and fewest natures (FIG. 26), as compared with the best performing scenario, dual token with bias.
Figure 26:
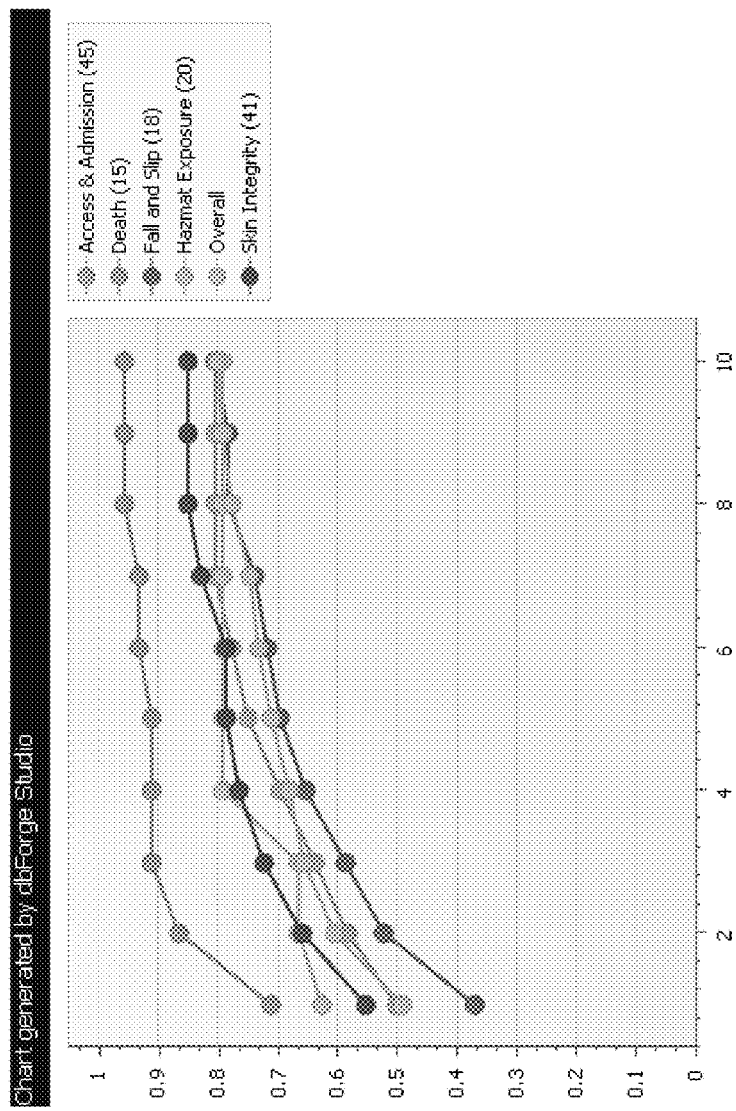

The exemplary graphs of FIGS. 25 and 26 show graph 2500 and 2600, respectively, which depict the confidence of classification within the five event types with the most natures, as compared with the best performing scenario, dual token with bias.

Comparing these measurements against the overall performance, the number of natures may not have a predictable impact on the confidence. For example, four of the five event types with the most natures performed better than the overall confidence measure. An exception is Clinical Event. Indeed, more general categories such as "clinical event" may include more general terms that appear on multiple classifications within the event type, whereas a more specific and descriptive even type such as "Laboratory Event" performs very well, likely due to the presence of more specialized tokens that appear on one or only a few classifications.

The system 105 may also be configured to adjust for new taxonomies/classifications. This adjustment or variation may have an impact on established confidence calculations. The system 105 may not weight these classifications as heavily for a variety of reasons. First, new taxonomy mapping may be incomplete. For example, there are numerous classifications present in the training corpus that may not have reverse mappings in the first pass taxonomy used to take these measurements. Using the examples above, roughly 250K events may have no mapping, and so may not be considered in either statistics, or confidence measurement.

The new taxonomy mapping may only use, for example, the patient affected party type. The vast majority of events are patient affected party type, but the other measurements may include other affected party types, so comparisons to the other measurements are potentially somewhat skewed.

The scope information used for reasonableness filtering by the system 105 may be only an approximation based on a most-likely fit back to the original scope filters, so it may be incorrect in some areas. The measurements can be recalculated once the scope information is more accurately established.

Figure 27:
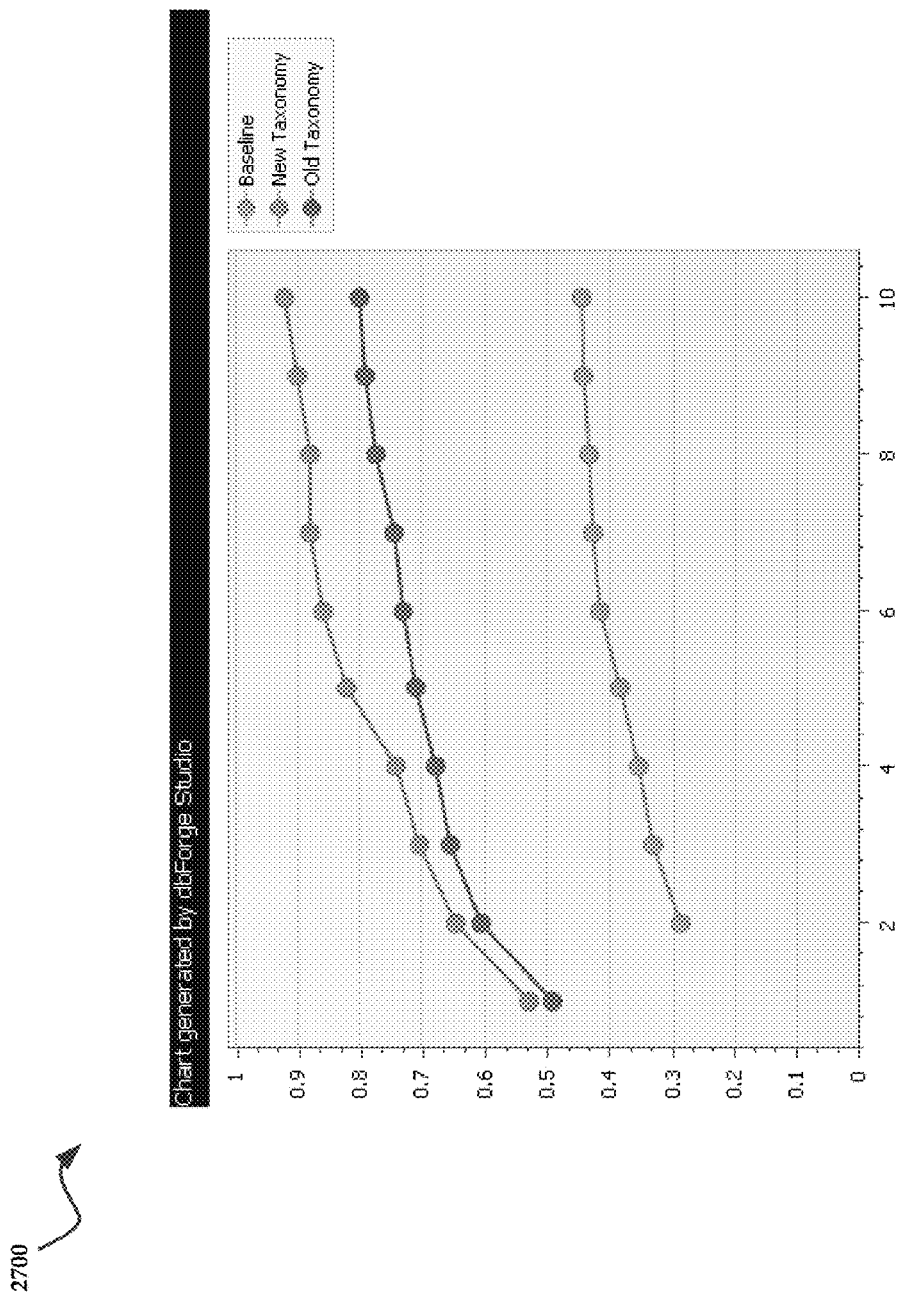
FIGS. 27 and 28 are graphs that collectively illustrate the impact of the new taxonomy on overall classification, as compared with the initial baseline, as well as the best measurement on the old taxonomy.
Figure 28:
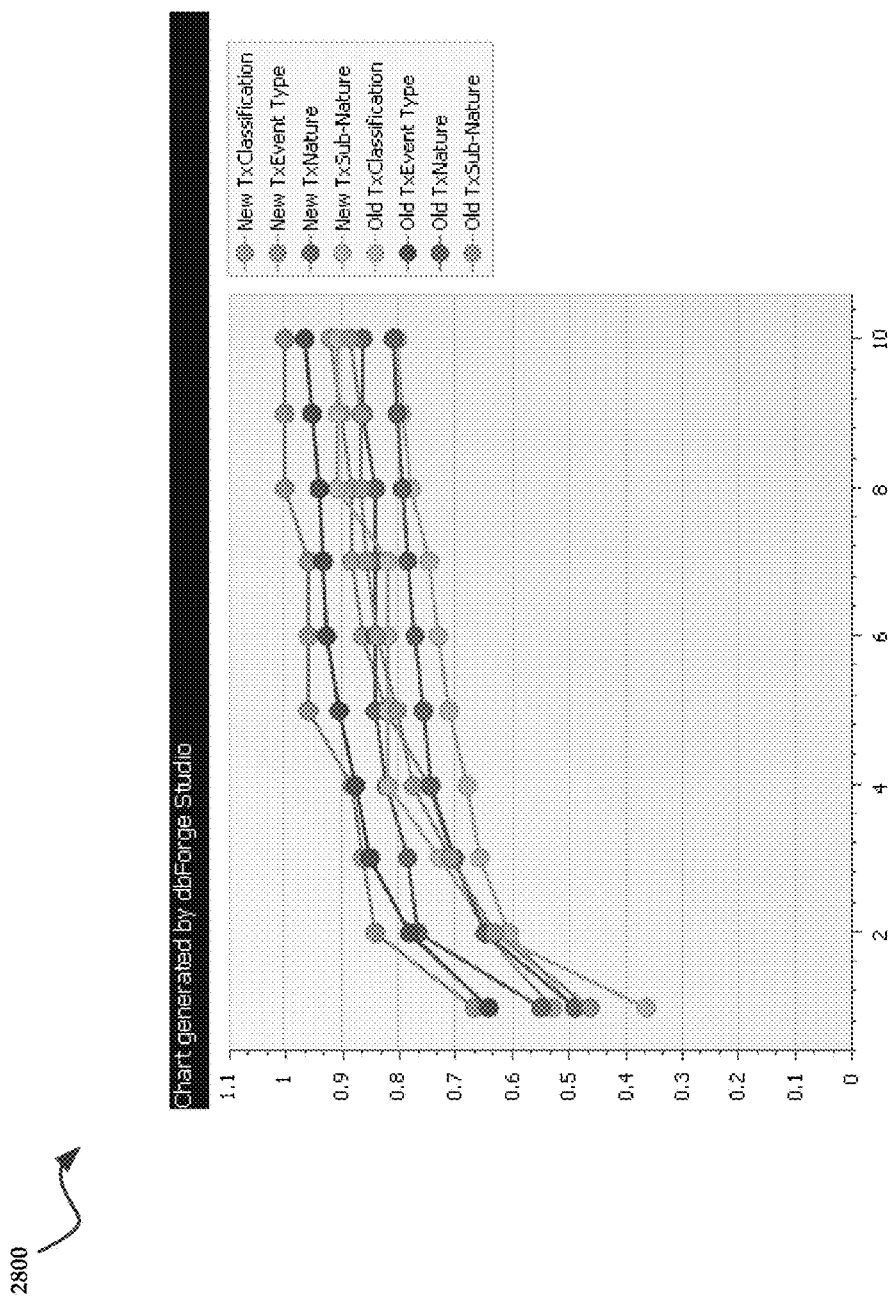

In light of the above, the following FIGS. 27 and 28 show graph 2700 and 2800, respectively, which collectively illustrate the impact of the new taxonomy on overall classification, as compared with the initial baseline, as well as the best measurement on the old taxonomy.

As mentioned above, the system 105 may execute the user interface module 125 (see FIG. 1) to generate various graphical user interfaces (GUIs) that allow users to interact with the functions of the system 105.

Figure 29:
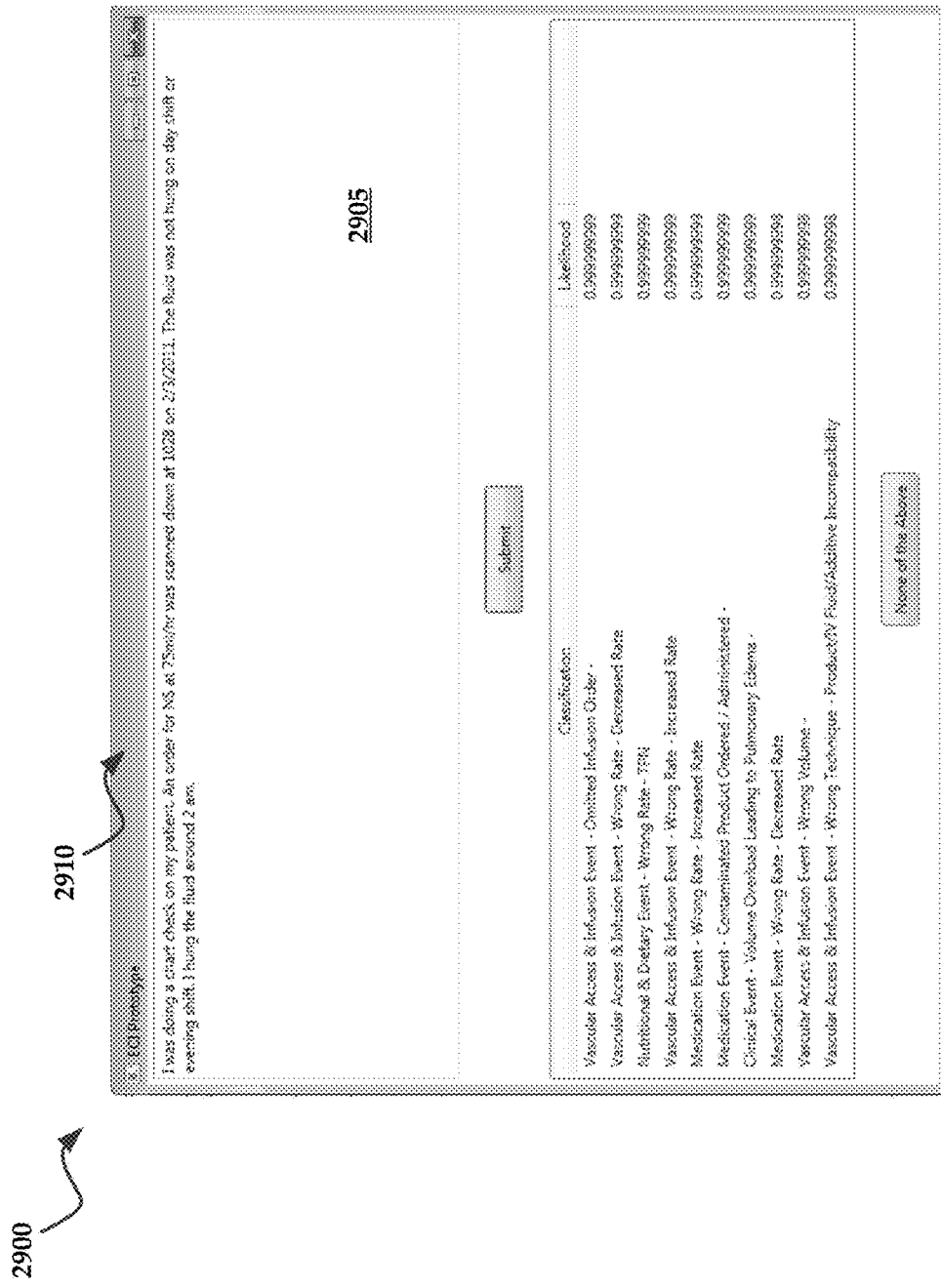
FIG. 29 is an exemplary GUI generated by the system of FIG. 1 that illustrates an approach to using the present technology within a safety event entry workflow.

FIG. 29 is an exemplary GUI 2900 generated by the system 105 that illustrates an approach to using the present technology within a safety event entry workflow. The user interface module 125 may output a display of the GUI 2900 an entry text box 2905, allowing a user to enter the narrative text 2910 for an event.

Figure 30:
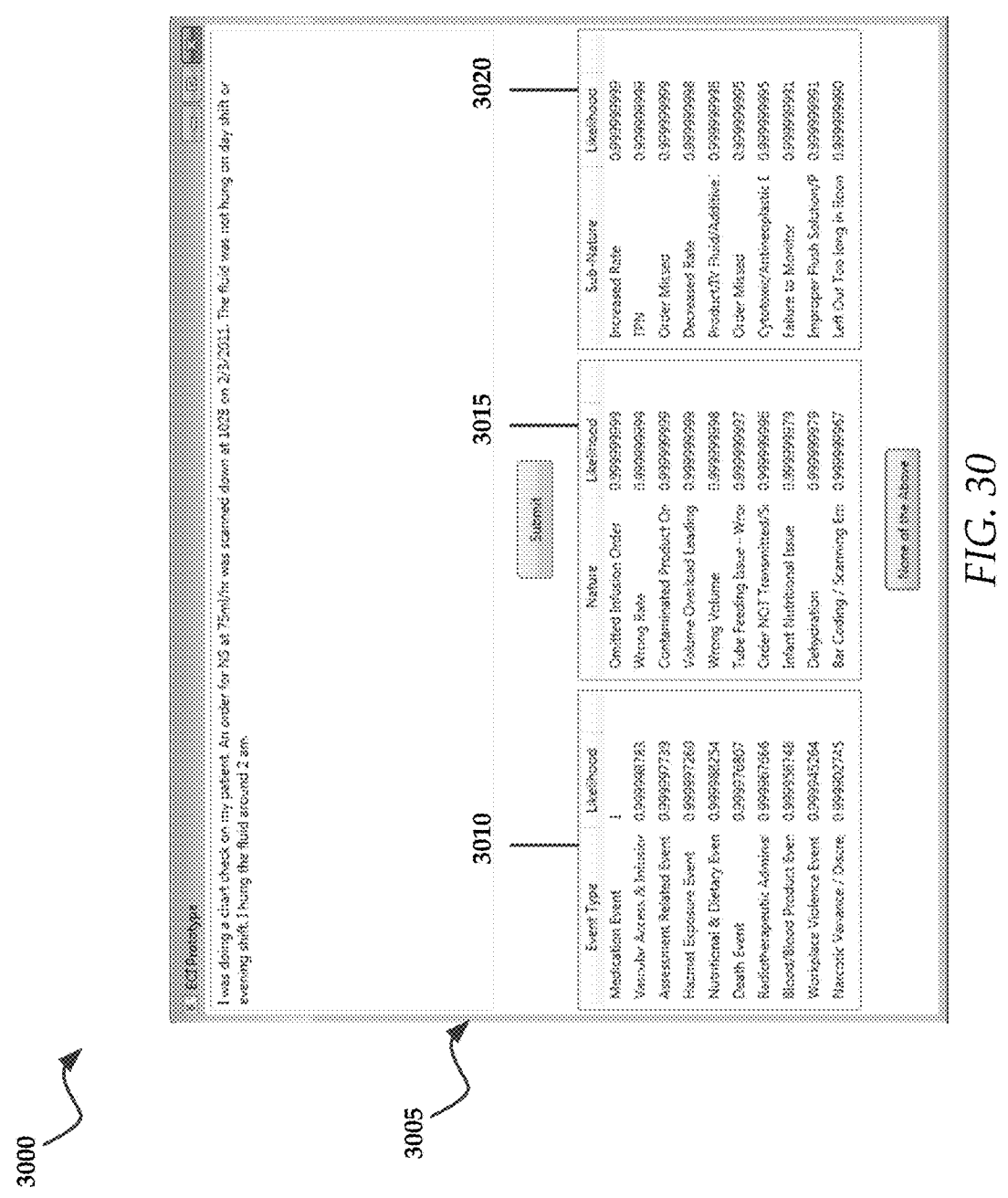

When the user clicks "submit" the user interface module 125 outputs the GUI 3000 of FIG. 30, which includes inferred suggestions 3005 for classification for the narrative text. If none of the suggestions match, pressing "None of the Above" may present the user with the suggested event types 3010, natures 3015, and sub-natures 3020 for the event text.

When the user selects a suggested classification, the system 105 may filter the list, removing the other two suggested classifications. For example, selecting the Order Missed sub-nature may cause the system 105 limit the suggestions in "event type" and "nature" to only those suggested classifications that have Order Missed as a valid sub-nature, as shown in the GUI 3100 of FIG. 31. Similarly, selecting the event type may filter the nature and sub-nature lists, and selecting a nature may filter the event type and sub-nature lists.

Figure 31:
FIG. 31 is an exemplary GUI generated by the system of FIG. 1 that illustrates a filtered list of classifications.

After receiving input via the various GUIs of FIGS. 29-31, the system 105 may return the top ten most likely suggestions for a given trait, or a plurality of traits.

In sum, with dual tokenization, trait bias, and preliminary mapping for the new taxonomy, the system 105 may achieve fairly good confidence for overall classification (70.6% within 3 suggestions, 92.2% confidence within ten suggestions). The quality of the tokens involved may be a good indicator of the confidence of the exemplary inference. It will be understood that because the system 105 can incorporate new taxonomies, the accuracy of the system 105 may improve over time. That is, the exemplary inference may guide users to the most appropriate selection, which in turn may reinforce the probabilities for the tokens involved.

In addition, the planned taxonomy streamlining may reduce the overall number of classifications, resulting in further improvements to accuracy. As demonstrated above, a reasonable approach may be to use suggested classification as a first pass, with suggested individual traits as a second pass, falling back to most frequently used, or even searches as a last resort.

Further investigation can also be performed, including simple investigation along the lines of probabilities within dimensions (such as care setting and affected party type), as well as more involved investigation such as the application of more sophisticated modeling techniques such as Latent Semantic Analysis (LSA).

Generally speaking, LSA is a statistical model of language learning and representation that uses vector averages in semantic space to assess the similarity between words or texts. LSA is well understood for determining similarity of documents by forming semantic concepts, and similarity is measured by the angle between the vectors. The system 105 may use LSA in a manner similar to a Bayesian approach. First, the system 105 may normalize the text for spelling, dictionary or domain usage, and synonyms (LSA has strategies within the algorithms for dealing with the issues of polysemy and synonymy). In various embodiments, the normalization may include automatically a) spell checking a narrative, b) identifying synonyms for key terms in the narrative, and c) reducing terms into a common key term. The synonym identification may include both common synonyms for words (e.g., for non-technical language) and using more specific terminology (e.g., phrases from a medical dictionary) that is unique to the context being classified. Also, terms may be combined into a single or common term, either by using contractions or by using well-known terms as a substitute for a description in the narrative. The reduction in terms may be accomplished using a technical dictionary, such as a medical dictionary, to assist in identifying phrases that are candidates for reduction in terms.

The system 105 may be configured to form vector representations of existing events. A vector representation of the current narrative is then created by the system 105 from the source text. Next, the system uses the vector representations to find a best match or best matches.

Figure 32A:
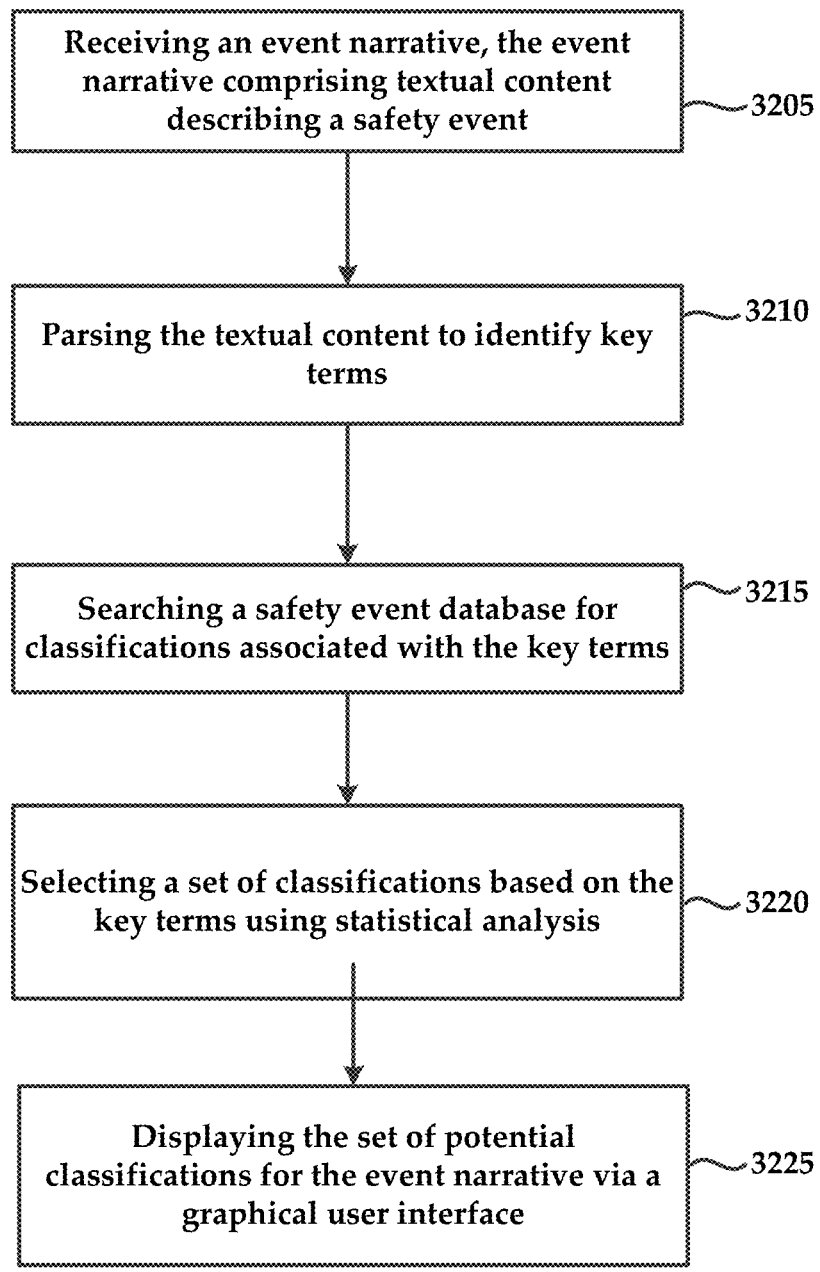
FIG. 32A is a flowchart of an example method that is executed in accordance with the present technology.

FIG. 32A is a flowchart of an example method that is executed in accordance with the present technology. According to some embodiments, the method may include receiving 3205 an event narrative, the event narrative comprising textual content describing a safety event. The event narrative may be input into a user interface or input as speech input and translated into text using a natural language parsing application or system.

Next, the method comprises parsing 3210 the textual content to identify key terms, as well as searching 3215 a safety event database for classifications associated with the key terms. Once classifications have been identified, the method may include selecting 3220 a set of classifications based on the key terms using statistical analysis. It will be understood that the set of classifications comprises potential event types for the event narrative.

Once the event types have been selected, the method includes displaying 3225 the set of classifications for the event narrative via a graphical user interface.

Figure 32B:
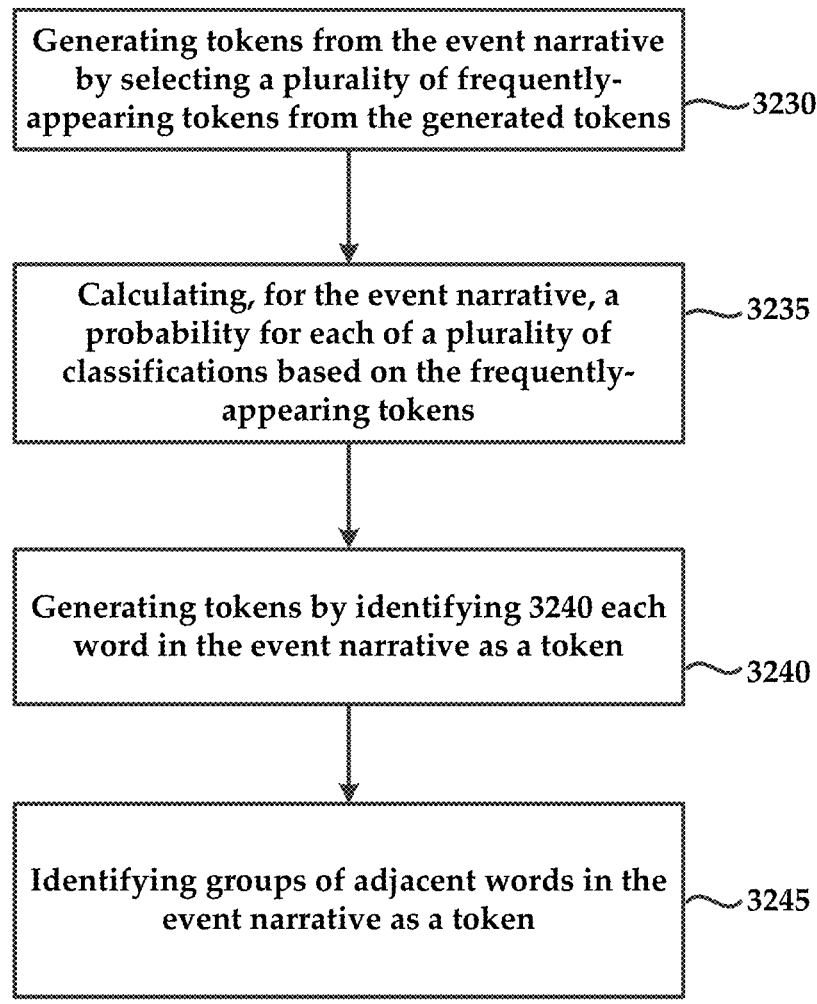
FIG. 32B is a flowchart of an exemplary parsing method that can be used with the method illustrated in FIG. 32A.

FIG. 32B is a flowchart of an exemplary parsing method that can be used with the method illustrated in FIG. 32A. For example, parsing can include generating tokens from the event narrative by selecting 3230 a plurality of frequently-appearing tokens from the generated tokens, the frequently-appearing tokens being tokens that appear most frequently in the event narrative. Next, the method includes calculating 3235, for the event narrative, a probability for each of a plurality of classifications based on the frequently-appearing tokens. To be sure, in one embodiment each frequently-appearing token comprises a corresponding probability for a classification. The selection of the set of classifications is based on the calculated probabilities.

According to some embodiments, the method includes generating tokens by identifying 3240 each word in the event narrative as a token and identifying 3245 groups of adjacent words in the event narrative as a token.

Figure 32C:
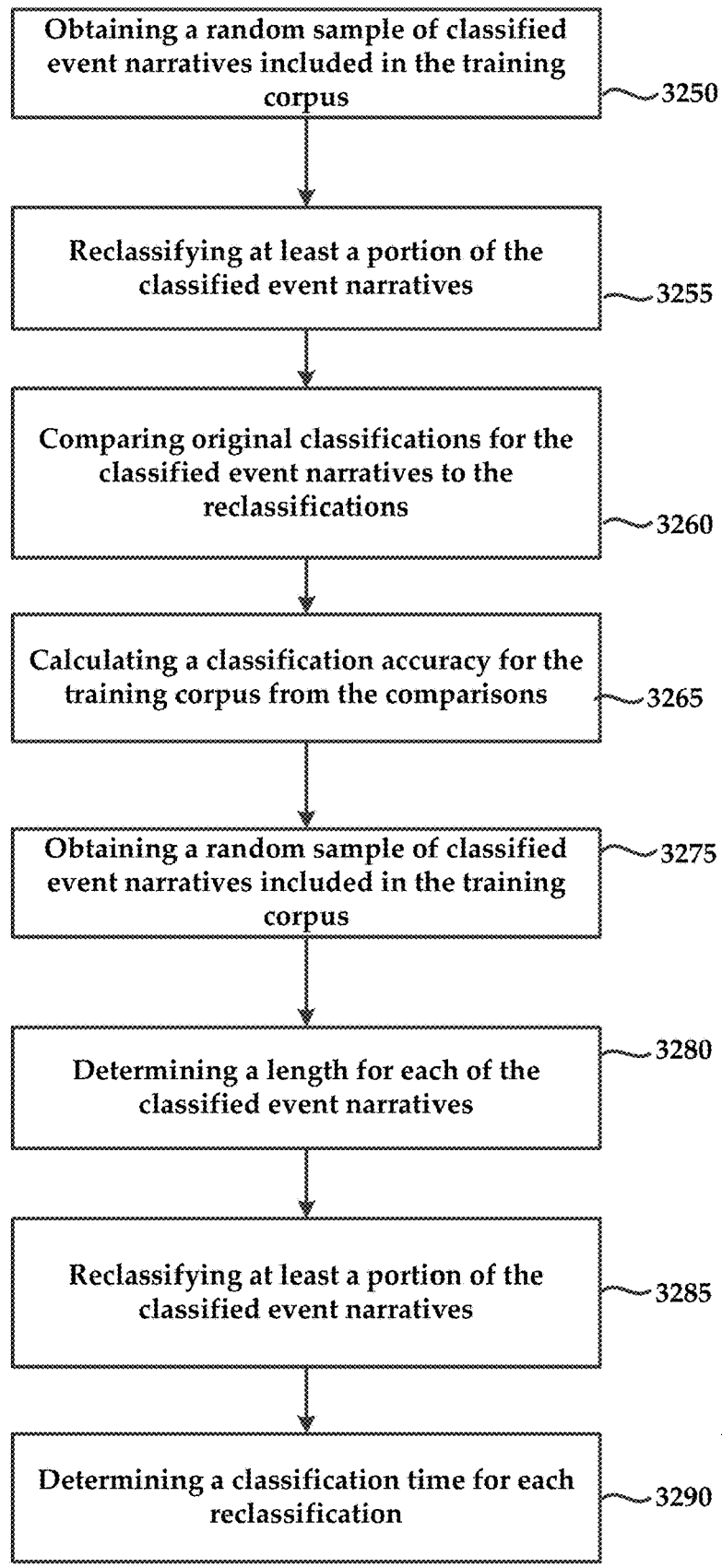
FIG. 32C illustrates an example method for verifying translation accuracy of a training corpus and further determining a classification efficiency.

FIG. 32C illustrates an example method for verifying translation accuracy of a training corpus and further determining a classification efficiency. This method may further define the probabilities calculated in the method of FIG. 32B.

For context, the probabilities described in the method of FIG. 32B are derived from a training corpus having a frequency distribution of the frequently-appearing tokens across the plurality of classifications. The method provides for verifying accuracy of the training corpus by obtaining 3250 a random sample of classified event narratives included in the training corpus and reclassifying 3255 at least a portion of the classified event narratives.

Next, the method includes comparing 3260 original classifications for the classified event narratives to the reclassifications and calculating 3265 a classification accuracy for the training corpus from the comparisons.

According to some embodiments determining a classification efficiency includes obtaining 3275 a random sample of classified event narratives included in the training corpus and determining 3280 a text length for each of the classified event narratives in the random sample.

In some embodiments the method includes reclassifying 3285 at least a portion of the classified event narratives in the random sample using the method illustrated in FIG. 32A, and then determining 3290 a classification time for each reclassification. Based on the text length and the classification time of each classified event narrative in the random sample, the method may include determining an expected response time for classifying event narratives (not shown).

Figure 33:
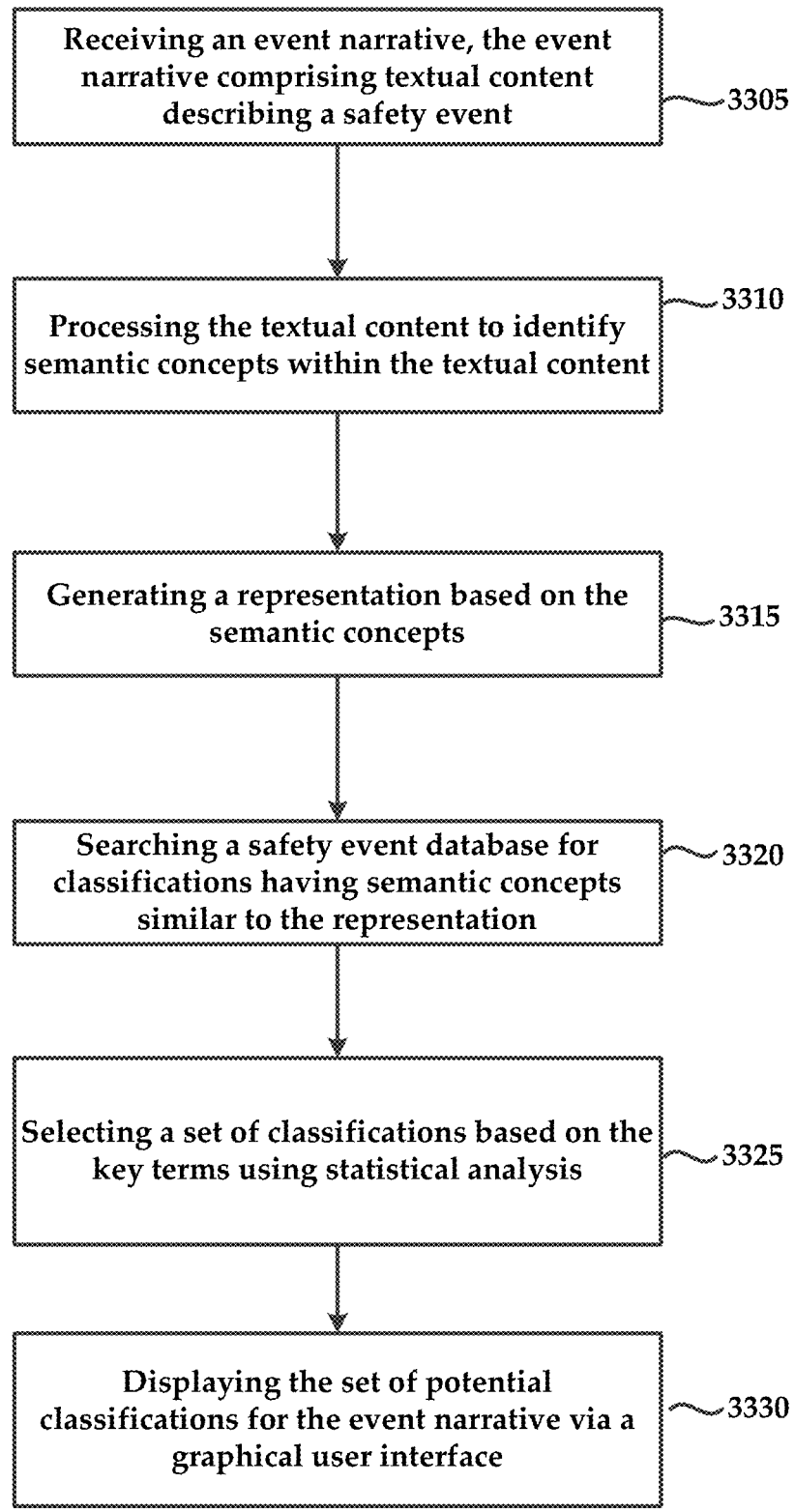
FIG. 33 is a flowchart of an exemplary method for classifying an event narrative.

FIG. 33 is a flowchart of an exemplary method for classifying an event narrative by receiving 3305 an event narrative. Next, the method includes processing 3310 the textual content to identify semantic concepts within the textual content.

In accordance with the present disclosure, the method also includes generating 3315 a representation based on the semantic concepts, as well as searching 3320 the safety event database for classifications having semantic concepts similar to the representation.

Once classifications for semantic concepts have been identified, the method further includes selecting 3325 a set of classifications based on the representation using semantic analysis and displaying 3330 the set of potential event types for the event narrative via a graphical user interface.

Figure 34:
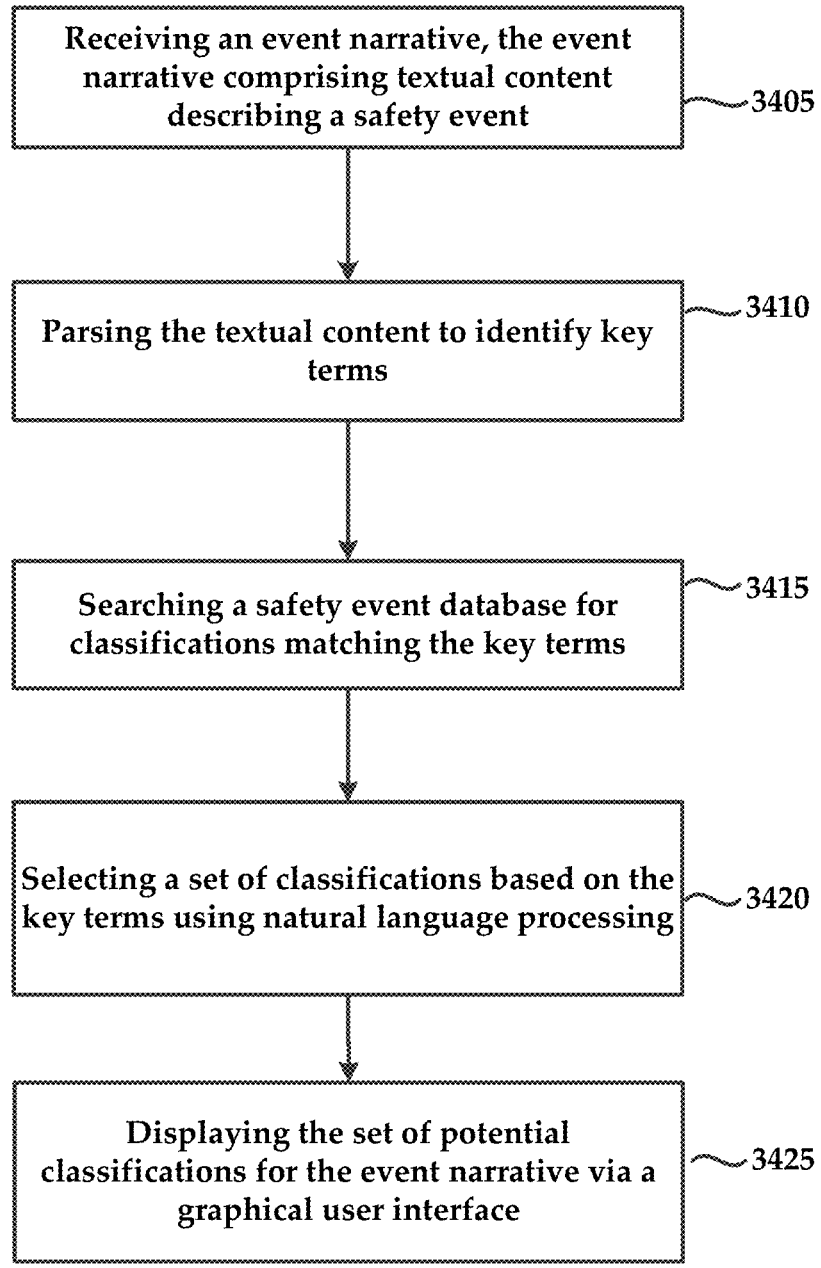
FIG. 34 is a flowchart of an exemplary method or classifying an event narrative.

FIG. 34 is a flowchart of an exemplary method or classifying an event narrative. In this embodiment, the method includes receiving 3405 an event narrative, where the event narrative includes textual content describing a safety event. The safety event will be understood to include an incident that has the potential to cause an adverse effect to a patient.

The method includes parsing 3410 the textual content to identify key terms within the textual content. As mentioned above, the key terms are linked to classifications for the event narrative. In some embodiments the classifications are stored in a safety event database. Next, the method includes searching 3415 the safety event database for classifications that match the key terms parsed from the textual content, as well as selecting 3420 a set of classifications based on the key terms using natural language processing analysis.

As with the other examples, the method includes displaying 3425 the set of potential event types for the event narrative via a graphical user interface.

While embodiments have been described above using statistical analysis and semantic analysis techniques, the present invention is not limited to these technologies. Any suitable technique or technology by which a narrative may be parsed for key terms may be used for the classification systems and methods described herein, including, for example, natural language processing analysis.

Figure 35:
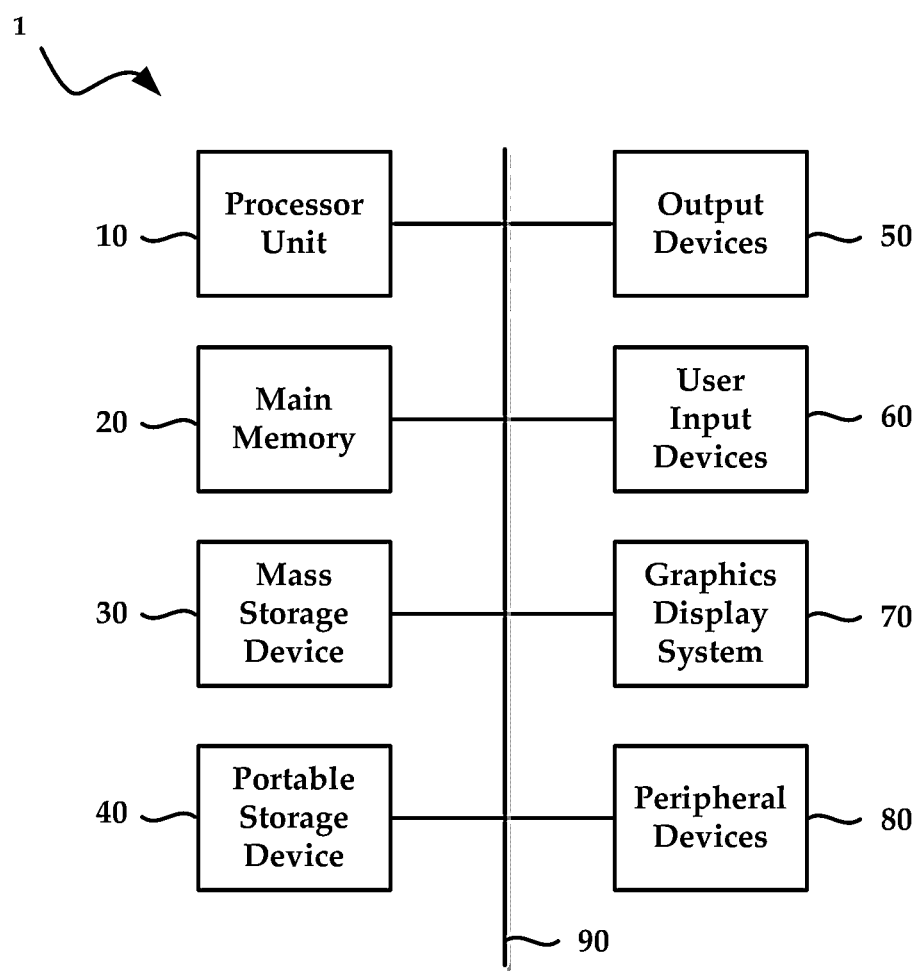
FIG. 35 illustrates an exemplary computing device that may be used to implement embodiments according to the present technology.

FIG. 35 illustrates an exemplary computing device 1 that may be used to implement an embodiment of the present systems and methods. The system 1 of FIG. 35 may be implemented in the contexts of the likes of clients, information display systems, computing devices, terminals, networks, servers, or combinations thereof. The computing device 1 of FIG. 35 includes a processor 10 and main memory 20. Main memory 20 stores, in part, instructions and data for execution by processor 10. Main memory 20 may store the executable code when in operation. The system 1 of FIG. 35 further includes a mass storage device 30, portable storage device 40, output devices 50, user input devices 60, a display system 70, and peripherals 80.

The components shown in FIG. 35 are depicted as being connected via a single bus 90. The components may be connected through one or more data transport means. Processor 10 and main memory 20 may be connected via a local microprocessor bus, and the mass storage device 30, peripherals 80, portable storage device 40, and display system 70 may be connected via one or more input/output (I/O) buses.

Mass storage device 30, which may be implemented with a magnetic disk drive or an optical disk drive, is a non-volatile storage device for storing data and instructions for use by processor 10. Mass storage device 30 can store the system software for implementing embodiments of the present technology for purposes of loading that software into main memory 20.

Portable storage device 40 operates in conjunction with a portable non-volatile storage medium, such as a floppy disk, compact disk or digital video disc, to input and output data and code to and from the computing system 1 of FIG. 35. The system software for implementing embodiments of the present technology may be stored on such a portable medium and input to the computing system 1 via the portable storage device 40.

Input devices 60 provide a portion of a user interface. Input devices 60 may include an alphanumeric keypad, such as a keyboard, for inputting alphanumeric and other information, or a pointing device, such as a mouse, a trackball, stylus, or cursor direction keys. Additionally, the system 1 as shown in FIG. 35 includes output devices 50. Suitable output devices include speakers, printers, network interfaces, and monitors.

Display system 70 may include a liquid crystal display (LCD) or other suitable display device. Display system 70 receives textual and graphical information, and processes the information for output to the display device. Peripherals 80 may include any type of computer support device to add additional functionality to the computing system. Peripherals 80 may include a modem or a router.

The components contained in the computing system 1 of FIG. 35 are those typically found in computing systems that may be suitable for use with embodiments of the present technology and are intended to represent a broad category of such computer components that are well known in the art. Thus, the computing system 1 can be a personal computer, hand held computing system, telephone, mobile computing system, workstation, server, minicomputer, mainframe computer, or any other computing system. The computer can also include different bus configurations, networked platforms, multi-processor platforms, etc. Various operating systems can be used including UNIX, Linux, Windows, Macintosh OS, Palm OS, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the technology. Those skilled in the art are familiar with instructions, processor(s), and storage media.

It is noteworthy that any hardware platform suitable for performing the processing described herein is suitable for use with the technology. The terms "computer-readable storage medium" and "computer-readable storage media" as used herein refer to any medium or media that participate in providing instructions to a CPU for execution. Such media can take many forms, including, but not limited to, non-volatile media, volatile media and transmission media. Non-volatile media include, for example, optical or magnetic disks, such as a fixed disk. Volatile media include dynamic memory, such as system RAM. Transmission media include coaxial cables, copper wire and fiber optics, among others, including the wires that comprise one embodiment of a bus. Transmission media can also take the form of acoustic or light waves, such as those generated during radio frequency (RF) and infrared (IR) data communications. Common forms of computer-readable media include, for example, a floppy disk, a flexible disk, a hard disk, magnetic tape, any other magnetic medium, a CD-ROM disk, digital video disk (DVD), any other optical medium, any other physical medium with patterns of marks or holes, a RAM, a PROM, an EPROM, an EEPROM, a FLASHEPROM, any other memory chip or data exchange adapter, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Computer program code for carrying out operations for aspects of the present technology may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the invention in the form disclosed. Many modifications and variations will be apparent to those of ordinary skill in the art without departing from the scope and spirit of the invention. Exemplary embodiments were chosen and described in order to best explain the principles of the present technology and its practical application, and to enable others of ordinary skill in the art to understand the invention for various embodiments with various modifications as are suited to the particular use contemplated.

Aspects of the present technology are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope

What is claimed is:

1. A method for classifying a safety event occurring in a healthcare setting using a classification system comprising an intelligent probabilistic event classification server having a hardware processor and a memory for storing executable instructions, the hardware processor being configured to execute the instructions to perform the method, comprising:

receiving on an interactive graphical user interface an event narrative, the event narrative comprising textual content describing a safety event;

parsing the textual content to identify key terms, the parsing comprising generating tokens from the event narrative by the hardware processor selecting a plurality of frequently-appearing tokens, the frequently-appearing tokens being tokens that appear most frequently in the event narrative, the parsing further comprising calculating, for the event narrative, a probability for each of a plurality of classifications based on the frequently-appearing tokens, each frequently-appearing token having a corresponding probability for a classification and representing an interesting token, the interesting token improving confidence and improving performance of the hardware processor of the intelligent probabilistic event classification server;

selecting a set of classifications, the set of classifications comprising potential event types for the event narrative, the selecting the set of classifications being based on the calculated probabilities;

the calculating probabilities comprising:
determining a number (NT) of occurrences of the token occurring in classified event narratives having a classification;
determining a number (NE) of classified event narratives having the classification;
determining a number (MT) of occurrences of the token relative to the classified event narratives not having the classification;
determining a number (ME) of events not associated with the classification; and
calculating a probability that a token is associated with a classification by:

$$\frac{NT/NE}{((NT/NE) + (MT/ME))}.$$

displaying the selected set of classifications on the interactive graphical user interface for a user selection from the selected set of classifications;

assigning the user selected classification to the event narrative; and using the user selected classification as feedback to improve accuracy of the classification system by reinforcing a corresponding probability for a classification for a frequently-appearing token.

2. The method of claim 1, the event narrative further comprising associated event metadata pertaining to one of: a patient identity, a time of the safety event, and a place of the safety event.

3. The method of claim 2, the associated event metadata comprising at least one of patient age, time of event, care setting, and gender.

4. The method of claim 1, further comprising normalizing the event narrative, the normalizing comprising automatically identifying synonyms to the key terms, and searching a safety event database for additional classifications that are associated with the synonyms.

5. The method according to claim 1, wherein generating tokens comprises any of:
identifying each word in the event narrative as a token; and
identifying groups of adjacent words in the event narrative as a token.

6. The method according to claim 1, the key terms being more highly weighted in the probability calculation when the key terms are identified as medical terms from a medical dictionary.

7. The method according to claim 1, further comprising:
determining a probability (PK) that a token is indicative of a selected classification; and
calculating a probability that a classification has been correctly classified for the event narrative by:

$$PT = \frac{\Pi PK}{\Pi PK + \Pi(1 - PK)}.$$

8. The method according to claim 7, further comprising:
computing a set of tokens included in the event narrative for a classification; and
utilizing the equation of claim 7 to combine probabilities of tokens in the event narrative into a probability for each classification.

9. The method according to claim 1, the probability being derived from a training corpus having a frequency distribution of the frequently-appearing tokens across the plurality of classifications, further comprising verifying accuracy of the training corpus by:
obtaining a random sample of classified event narratives included in the training corpus;
reclassifying at least a portion of the classified event narratives;
comparing original classifications for the classified event narratives to the reclassifications; and
calculating a classification accuracy for the training corpus from the comparisons.

10. The method according to claim 9, further comprising:
determining a number of event narratives that could not be reclassified; and
grouping the number of event narratives into a default classification.

11. The method according to claim 9, further comprising determining a classification efficiency by:
obtaining a random sample of classified event narratives included in the training corpus;
determining a text length for each of the classified event narratives in the random sample;
reclassifying at least a portion of the classified event narratives in the random sample using the method of claim 1;
determining a classification time for each reclassification; and
based on the text length and the classification time of each classified event narrative in the random sample, determining an expected response time for classifying event narratives.

12. The method according to claim 1, further comprising analyzing one of a plurality of metrics for the event narrative, the plurality of metrics comprising a care setting, a department, a geographical location, a nature within an event type, a sub-nature within an event type, a sub-nature within an event type and a nature, an event type within a nature, and an event type within a nature and a sub-nature.

13. The method according to claim 12, further comprising adjusting a corresponding probability of a token having a classification based on the user selected classification.

14. The method of claim 1, further comprising normalizing the event narrative, the normalizing comprising automatically reducing multiple terms into a common key term, and searching a safety event database for additional classifications that are associated with the common key term.

* * * * *